United States Patent
Omori et al.

(10) Patent No.: US 10,646,612 B2
(45) Date of Patent: May 12, 2020

(54) POLYACRYLIC ACID (SALT) WATER ABSORBENT, AND METHOD FOR PRODUCING SAME

(71) Applicant: NIPPON SHOKUBAI CO., LTD., Osaka-shi, Osaka (JP)

(72) Inventors: Kohei Omori, Himeji (JP); Kazushi Torii, Himeji (JP); Nobuya Tanaka, Himeji (JP); Yusuke Watanabe, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 15/106,109

(22) PCT Filed: Dec. 19, 2014

(86) PCT No.: PCT/JP2014/083697
§ 371 (c)(1),
(2) Date: Jun. 17, 2016

(87) PCT Pub. No.: WO2015/093594
PCT Pub. Date: Jun. 25, 2015

(65) Prior Publication Data
US 2016/0375171 A1 Dec. 29, 2016

(30) Foreign Application Priority Data
Dec. 20, 2013 (JP) ................................. 2013-263531

(51) Int. Cl.
*A61L 15/26* (2006.01)
*B01J 20/18* (2006.01)
(Continued)

(52) U.S. Cl.
CPC ............... *A61L 15/26* (2013.01); *A61L 15/60* (2013.01); *B01J 20/18* (2013.01); *B01J 20/261* (2013.01);
(Continued)

(58) Field of Classification Search
CPC . A61L 15/26; A61L 15/60; B01J 20/18; B01J 20/261; B01J 20/267; B01J 20/3085;
(Continued)

(56) References Cited

U.S. PATENT DOCUMENTS 4,703,067 A 10/1987 Mikita et al.
4,734,478 A 3/1988 Tsubakimoto et al.
(Continued)

FOREIGN PATENT DOCUMENTS

EP 0450922 A2 10/1991
EP 0595803 A1 5/1994
(Continued)

OTHER PUBLICATIONS

European Search Report dated Jun. 28, 2017 issued in European Patent Application No. 14872466.9.
(Continued)

*Primary Examiner* — William K Cheung
(74) *Attorney, Agent, or Firm* — Harness Dickey & Pierce P.L.C.

(57) ABSTRACT

Provided is a water-absorbing agent which is less likely to cause gel blocking and is suitable for a sanitary product and an absorbent article each being thin and containing a large amount of a water-absorbing agent, and which, while maintaining or hardly losing the other physical properties (a fluid retention capacity and a bulk specific gravity) of the water-absorbing agent, simultaneously achieves a high water absorbing speed (e.g., FSR), a high fluid retention capacity under load, high liquid permeability, and salt tolerance. The
(Continued)

water-absorbing agent is a polyacrylic acid (salt)-based water-absorbing agent whose surface and its vicinity are crosslinked by an organic surface crosslinking agent, characterized by satisfying the following (A)-(D): (A) Free Swell Rate (FSR) of at least 0.28 g/g/s, or Absorption Time (Vortex) of 42 seconds or less; (B) Absorption Against Pressure (AAP) of at least 20 g/g; (C) Salt Tolerance Index represented by "Salt Tolerance Index=(CRCdw)/(CRCs)" where CRCdw is a centrifuge retention capacity (unit; g/g) for deionized water (dw), and CRCs is a centrifuge retention capacity (unit; g/g) for a 0.9 weight % saline, satisfying "Salt Tolerance Index≤0.49×CRCs−7.47"; and (D) Bulk Specific Gravity of 0.55 to 0.70 g/cm$^3$.

6 Claims, 1 Drawing Sheet

(51) Int. Cl.
  *A61L 15/60* (2006.01)
  *C08J 3/24* (2006.01)
  *B01J 20/26* (2006.01)
  *B01J 20/30* (2006.01)

(52) U.S. Cl.
  CPC ......... *B01J 20/267* (2013.01); *B01J 20/3085* (2013.01); *C08J 3/24* (2013.01); *B01J 2220/46* (2013.01); *B01J 2220/68* (2013.01); *C08J 2333/02* (2013.01)

(58) Field of Classification Search
  CPC ............... B01J 2220/46; B01J 2220/68; B01J 2333/02; C08J 3/24
  USPC ..................................................... 525/329.7
  See application file for complete search history.

(56) References Cited

U.S. PATENT DOCUMENTS

| | | |
|---|---|---|
| 4,755,562 A | 7/1988 | Alexander et al. |
| 4,783,510 A | 11/1988 | Saotome |
| 4,824,901 A | 4/1989 | Alexander et al. |
| 5,002,986 A | 3/1991 | Fujiura et al. |
| 5,124,188 A | 6/1992 | Roe et al. |
| 5,154,713 A | 10/1992 | Lind |
| 5,314,420 A | 5/1994 | Smith et al. |
| 5,399,591 A | 3/1995 | Smith et al. |
| 5,409,771 A | 4/1995 | Dahmen et al. |
| 5,451,613 A | 9/1995 | Smith et al. |
| 5,462,972 A | 10/1995 | Smith et al. |
| 5,610,208 A | 3/1997 | Dairoku et al. |
| 5,624,967 A | 4/1997 | Hitomi et al. |
| 5,672,633 A | 9/1997 | Brehm et al. |
| 5,712,316 A | 1/1998 | Dahmen et al. |
| 5,856,370 A | 1/1999 | Chmelir |
| 5,985,944 A | 11/1999 | Ishizaki et al. |
| 6,107,358 A | 8/2000 | Harada et al. |
| 6,136,873 A | 10/2000 | Hahnle et al. |
| 6,150,469 A | 11/2000 | Harada et al. |
| 6,239,230 B1 | 5/2001 | Eckert et al. |
| 6,265,488 B1 | 7/2001 | Fujino et al. |
| 6,297,319 B1 | 10/2001 | Nagasuna et al. |
| 6,297,335 B1 | 10/2001 | Funk et al. |
| 6,372,852 B2 | 4/2002 | Hitomi et al. |
| 6,472,478 B1 | 10/2002 | Funk et al. |
| 6,559,239 B1 | 5/2003 | Riegel et al. |
| 6,605,673 B1 | 8/2003 | Mertens et al. |
| 6,620,889 B1 | 9/2003 | Mertens et al. |
| 6,657,015 B1 | 12/2003 | Riegel et al. |
| 6,750,262 B1 | 6/2004 | Hahnle et al. |
| 6,809,158 B2 | 10/2004 | Ikeuchi et al. |
| 6,939,914 B2 | 9/2005 | Qin et al. |
| 7,201,941 B2 | 4/2007 | Irie et al. |
| 2002/0128618 A1 | 9/2002 | Frenz et al. |
| 2002/0165288 A1 | 11/2002 | Frenz et al. |
| 2004/0071966 A1 | 4/2004 | Inger et al. |
| 2004/0176544 A1 | 9/2004 | Mertens et al. |
| 2004/0176557 A1 | 9/2004 | Mertens et al. |
| 2005/0176834 A1 | 8/2005 | Hintz et al. |
| 2005/0221980 A1 | 10/2005 | Adachi et al. |
| 2007/0015860 A1 | 1/2007 | Frank |
| 2007/0161759 A1 | 7/2007 | Riegel et al. |
| 2007/0225422 A1* | 9/2007 | Sakamoto .................. C08F 2/44 524/458 |
| 2008/0281049 A1 | 11/2008 | Wendker et al. |
| 2010/0041550 A1 | 2/2010 | Riegel et al. |
| 2010/0268181 A1 | 10/2010 | Ziemer et al. |
| 2010/0308263 A1* | 12/2010 | Torii ........................ A61L 15/60 252/194 |
| 2011/0040044 A1 | 2/2011 | Motoyama et al. |
| 2011/0042612 A1 | 2/2011 | Riegel et al. |
| 2011/0112252 A1 | 5/2011 | Blei et al. |
| 2011/0313113 A1 | 12/2011 | Sakamoto et al. |
| 2012/0258851 A1 | 10/2012 | Nakatsuru et al. |
| 2013/0026412 A1 | 1/2013 | Machida et al. |
| 2013/0101851 A1 | 4/2013 | Takaai et al. |

FOREIGN PATENT DOCUMENTS

| | | |
|---|---|---|
| EP | 0819721 A1 | 1/1998 |
| EP | 0940149 A1 | 9/1999 |
| EP | 1 191 051 A2 | 3/2002 |
| EP | 1521601 A2 | 4/2005 |
| EP | 1824910 A2 | 8/2007 |
| JP | 1-318021 | 12/1989 |
| JP | 4-46617 | 2/1992 |
| JP | 9-268232 | 10/1997 |
| JP | 2003-238696 A | 8/2003 |
| JP | 2004522491 A | 7/2004 |
| JP | 2004-290960 A | 10/2004 |
| JP | 2007-284675 A | 11/2007 |
| JP | 2009-268232 | 12/2009 |
| JP | 2011527360 A | 10/2011 |
| JP | 2014/083697 A | 5/2014 |
| KR | 2011/0049072 A | 5/2011 |
| WO | WO-91/15362 A1 | 10/1991 |
| WO | WO-91/15368 A1 | 10/1991 |
| WO | WO-92/000108 A1 | 1/1992 |
| WO | WO-92/18171 A1 | 10/1992 |
| WO | WO-94/022502 A1 | 10/1994 |
| WO | WO-95/02002 A1 | 1/1995 |
| WO | WO-95/020002 A1 | 7/1995 |
| WO | WO-95126209 A1 | 10/1995 |
| WO | WO-97/017397 A1 | 5/1997 |
| WO | WO-98149221 A1 | 11/1998 |
| WO | WO-00/46260 A1 | 8/2000 |
| WO | WO-00/052087 A1 | 9/2000 |
| WO | WO-00/53644 A1 | 9/2000 |
| WO | WO-00/53664 A1 | 9/2000 |
| WO | WO-01/074913 A1 | 10/2001 |
| WO | WO-02/22717 A1 | 3/2002 |
| WO | WO-02120068 A1 | 3/2002 |
| WO | WO 02/100451 A2 | 12/2002 |
| WO | WO-2005/012406 A1 | 2/2005 |
| WO | WO-2005/063313 A1 | 7/2005 |
| WO | WO-2005/080479 A1 | 9/2005 |
| WO | WO-2006033477 A1 | 3/2006 |
| WO | WO-2006/062258 A2 | 6/2006 |
| WO | WO-2007/065834 A1 | 6/2007 |
| WO | WO-2006/092842 A1 | 8/2008 |
| WO | WO-2008/092843 A1 | 8/2008 |
| WO | WO-2008/110524 A1 | 9/2008 |
| WO | WO-2009/062902 A2 | 5/2009 |
| WO | WO-2009/080611 A2 | 7/2009 |
| WO | WO-091125849 A1 | 10/2009 |
| WO | WO-2010/095427 A1 | 8/2010 |
| WO | WO-2011/078298 A1 | 6/2011 |

(56) References Cited

FOREIGN PATENT DOCUMENTS

WO   WO-2011/117263 A1   9/2011
WO   WO-2011126079 A1    10/2011

OTHER PUBLICATIONS

International Search Report of PCT/JP2014/083697, dated Mar. 2015.
English Translation of International Preliminary Report on Patentability of PCT/JP2014083697, dated Mar. 2015.
"Modern Superabsorbant Polymer Technology", 1998, pp. 39-44, pp. 97-103, pp. 197-199, etc.

* cited by examiner

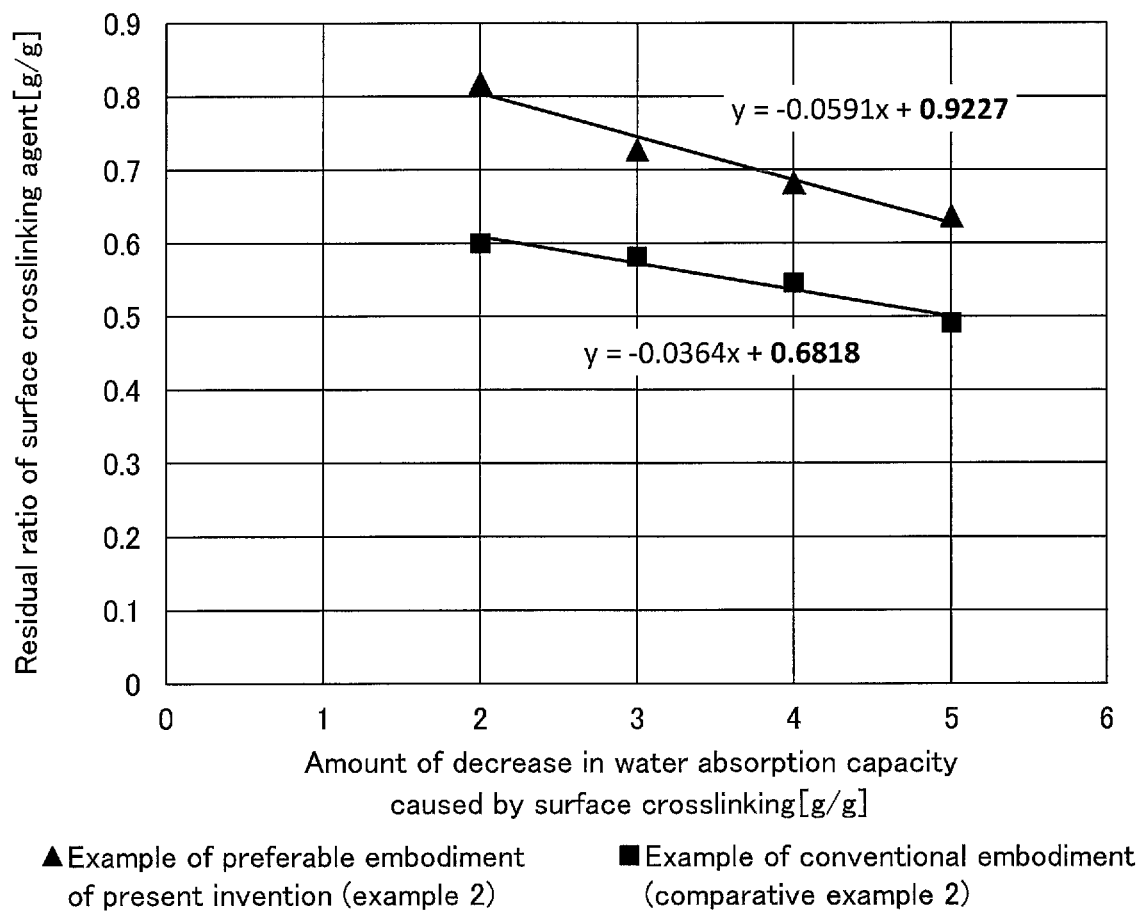

POLYACRYLIC ACID (SALT) WATER ABSORBENT, AND METHOD FOR PRODUCING SAME

CROSS-REFERENCE TO RELATED APPLICATIONS

This patent application is a U.S. national stage filing under 35 U.S.C. § 371 of International Application No. PCT/JP2014/083697 filed on of 19 Dec. 2014, which claims priority to Japanese Patent Application No. 2013-263531 filed on 20 Dec. 2013. The entire disclosures of each of the above recited applications are incorporated herein by reference.

TECHNICAL FIELD

The present invention relates to a polyacrylic acid (salt)-based water-absorbing agent and to a method for producing the polyacrylic acid (salt)-based water-absorbing agent. More specifically, the present invention relates to, for example, (i) a water-absorbing agent to be used in sanitary products such as disposable diapers, sanitary napkins, and incontinence pads and (ii) a method for producing the water-absorbing agent.

BACKGROUND ART

Currently, an absorbent body that is made of a water-absorbing agent that is made mainly from, for example, hydrophilic fiber such as pulp and acrylic acid (salt) is widely used in sanitary products such as disposable diapers, sanitary napkins, and incontinence pads so that bodily fluids are absorbed. In recent years, these sanitary products such as disposable diapers, sanitary napkins, and incontinence pads have been made higher in functionality and thinner, so that a larger amount of a water-absorbing agent tends to be used in a piece of sanitary product, and a water-absorbing agent tends to be contained in a larger amount with respect to an entire absorbent body that is made of, for example, a water-absorbing agent and hydrophilic fiber. Specifically, study has been carried out on a reduction in thickness of a sanitary product without a reduction in amount of water absorption by increasing a water-absorbing agent content in an absorbent body by (i) using a smaller amount of hydrophilic fiber having a small bulk specific gravity and (ii) using a larger amount of a water-absorbing agent having excellent water absorbency and a large bulk specific gravity.

Though such a sanitary product, in which a water-absorbing agent content is increased by decreasing a percentage of hydrophilic fiber, tends to be preferable from the viewpoint of simply storing a liquid, a problem rather arises in consideration of distribution and diffusion of a liquid in actual use of the sanitary product.

A water-absorbing agent that absorbs water turns to a soft gel-like water-absorbing agent. Thus, in a case where such a water-absorbing agent that is large in amount per unit volume absorbs water, a gel blocking phenomenon occurs. This phenomenon causes a considerable reduction in diffusibility of a liquid in a sanitary product. As a result, a part of the water-absorbing agent, which part is distant from a central area of the sanitary product and is therefore difficult for the liquid to reach, does not effectively function. This prevents an effect of increasing a water-absorbing agent content from being sufficiently exhibited, so that the sanitary product in actual use has absorbing ability that is much lower than a theoretical level.

In order that such a problem is avoided and absorbing ability of an absorbent body is maintained, a range of a ratio between hydrophilic fiber and a water-absorbing agent is inevitably restricted, so that thinning of sanitary products is also limited.

Examples of indices used to evaluate an improvement in gel blocking in a sanitary product encompass a fluid retention capacity under load (Absorbency Against Pressure (AAP) or Performance Under Pressure (PUP)), indicative of a water absorbent property under load, a saline flow conductivity (hereinafter abbreviated as "SFC"; see Patent Literature 1) and the like.

As a well-known technique for improving gel blocking, there have been known the following techniques: a technique in which crosslinking densities inside and outside of a water-absorbing agent are changed by a surface treatment; a technique for combining a surface treatment with (i) inorganic compound(s) as a liquid permeability improving agent, such as an inorganic microparticle and a polyvalent metal salt and/or (ii) cationic polymer compound(s) as a liquid permeability improving agent; a technique for improving water absorption performance, particularly liquid diffusibility; and a technique for controlling a reaction environment of a surface crosslinking treatment (see Patent Literatures 2 to 40). There have also been proposed various improvement techniques related to surface crosslinking (see Patent Literatures 72 to 74).

Meanwhile, not only liquid permeability but also water absorbing speed is also an important fundamental physical property of a water-absorbing agent. As a method for improving the water absorbing speed, there is known a technique for improving the water absorbing speed by increasing a specific surface area. Specific proposed examples of such a technique encompass a technique for minutely controlling a particle diameter, a technique for granulating fine powder having a large surface area, a technique for causing a hydrogel to be porous by freeze-drying, a technique for surface-crosslinking particles while granulating the particles, a technique for increasing a surface area of gel particles during gel grinding, foaming polymerization techniques such as introduction of microbubbles and addition of a surfactant, a technique for carrying out foaming and crosslinking after polymerization (see Patent Literatures 41 to 71), and the like.

An invention of a water-absorbing agent which simultaneously achieves the liquid permeability, the fluid retention capacity under load, and the water absorbing speed is necessary for development of sanitary products including an absorbent body that is thin and excellent in water absorbing speed. In general, the water absorbing speed and the specific surface area have a positive correlation, and the liquid permeability and the specific surface area have a negative correlation. This makes it extremely difficult to achieve both an increase in water absorbing speed that greatly depends on the surface area and an increase in liquid permeability and fluid retention capacity. Further, for improvement in water absorbing speed, there has been proposed a technique for making a water-absorbing agent porous (e.g., foaming polymerization). However, the water-absorbing agent that has been made porous has a smaller bulk specific gravity. Thus, the above technique not only causes an increase in transport cost and storage cost but also runs counter to thinning of sanitary products.

Further, society has recently been aging in advanced countries, and an elderly generation uses sanitary products such as disposable diapers at such a high rate that the elderly generation and infants are equally matched in usage rate of those sanitary products. Under the circumstances, a concentration of urine to be absorbed by sanitary products varies from a low concentration to a high concentration, and a water-absorbing agent is required to have water absorption performance called salt tolerance that is independent of salt concentration.

CITATION LIST

Patent Literatures

[Patent Literature 1]
Pamphlet of International Publication No. WO 95/26209
[Patent Literature 2]
Specification of U.S. Pat. No. 6,297,319
[Patent Literature 3]
Specification of U.S. Pat. No. 6,372,852
[Patent Literature 4]
Specification of U.S. Pat. No. 6,265,488
[Patent Literature 5]
Specification of U.S. Pat. No. 6,809,158
[Patent Literature 6]
Specification of U.S. Pat. No. 4,734,478
[Patent Literature 7]
Specification of U.S. Pat. No. 4,755,562
[Patent Literature 8]
Specification of U.S. Pat. No. 4,824,901
[Patent Literature 9]
Specification of U.S. Pat. No. 6,239,230
[Patent Literature 10]
Specification of U.S. Pat. No. 6,559,239
[Patent Literature 11]
Specification of U.S. Pat. No. 6,472,478
[Patent Literature 12]
Specification of U.S. Pat. No. 6,657,015
[Patent Literature 13]
Specification of U.S. Pat. No. 5,672,633
[Patent Literature 14]
Specification of European Patent Application Publication No. 0940149
[Patent Literature 15]
Pamphlet of International Publication No. WO 2006/033477
[Patent Literature 16]
Specification of U.S. Pat. No. 7,201,941
[Patent Literature 17]
Specification of U.S. Pat. No. 4,783,510
[Patent Literature 18]
Specification of European Patent No. 1824910
[Patent Literature 19]
Pamphlet of International Publication No. WO 2002/100451
[Patent Literature 20]
Specification of U.S. Pat. No. 5,610,208
[Patent Literature 21]
Pamphlet of International Publication No. WO 92/000108
[Patent Literature 22]
Pamphlet of International Publication No. WO 98/49221
[Patent Literature 23]
Pamphlet of International Publication No. WO 00/53644
[Patent Literature 24]
Pamphlet of International Publication No. WO 00/53664
[Patent Literature 25]
Pamphlet of International Publication No. WO 01/074913
[Patent Literature 26]
Pamphlet of International Publication No. WO 2002/020068
[Patent Literature 27]
Pamphlet of International Publication No. WO 2002/022717
[Patent Literature 28]
Pamphlet of International Publication No. WO 2005/080479
[Patent Literature 29]
Pamphlet of International Publication No. WO 2007/065834
[Patent Literature 30]
Pamphlet of International Publication No. WO 2008/092842
[Patent Literature 31]
Pamphlet of International Publication No. WO 2008/092843
[Patent Literature 32]
Pamphlet of International Publication No. WO 2008/110524
[Patent Literature 33]
Pamphlet of International Publication No. WO 2009/080611
[Patent Literature 34]
Japanese Examined Patent Application Publication, Tokukouhei, No. 4-46617 (1992)
[Patent Literature 35]
Pamphlet of International Publication No. WO 00/46260
[Patent Literature 36]
Specification of European Patent No. 1191051
[Patent Literature 37]
Pamphlet of International Publication No. WO 2011/117263
[Patent Literature 38]
Pamphlet of International Publication No. WO 09/125849
[Patent Literature 39]
Specification of Korean Patent No. 2011/0049072
[Patent Literature 40]
Japanese Translation of PCT Patent Application Publication, Tokuhyo, No. 2011-527360
[Patent Literature 41]
Pamphlet of International Publication No. WO 92/18171
[Patent Literature 42]
Specification of U.S. Pat. No. 5,624,967
[Patent Literature 43]
Pamphlet of International Publication No. WO 2005/012406
[Patent Literature 44]
Specification of U.S. Pat. No. 5,002,986
[Patent Literature 45]
Specification of U.S. Pat. No. 6,939,914
[Patent Literature 46]
Specification of U.S. Pat. No. 5,124,188
[Patent Literature 47]
Specification of European Patent No. 0595803
[Patent Literature 48]
Specification of European Patent No. 0450922
[Patent Literature 49]
Pamphlet of International Publication No. WO 91/15368
[Patent Literature 50]
Specification of U.S. Pat. No. 5,154,713
[Patent Literature 51]
Specification of U.S. Pat. No. 5,314,420
[Patent Literature 52]
Specification of U.S. Pat. No. 5,399,591
[Patent Literature 53]
Specification of U.S. Pat. No. 5,451,613
[Patent Literature 54]
Specification of U.S. Pat. No. 5,462,972
[Patent Literature 55]
Pamphlet of International Publication No. WO 95/02002
[Patent Literature 56]
Pamphlet of International Publication No. WO 2005/063313
[Patent Literature 57]
Pamphlet of International Publication No. WO 94/022502
[Patent Literature 58]
Specification of U.S. Pat. No. 4,703,067
[Patent Literature 59]
Pamphlet of International Publication No. WO 97/017397
[Patent Literature 60]
Pamphlet of International Publication No. WO 00/052087

[Patent Literature 61]
Specification of U.S. Pat. No. 6,107,358
[Patent Literature 62]
Specification of U.S. Pat. No. 5,856,370
[Patent Literature 63]
Specification of U.S. Pat. No. 5,985,944
[Patent Literature 64]
Pamphlet of International Publication No. WO 2009/062902
[Patent Literature 65]
Specification of U.S. Patent Application Publication No. 2007/0225422
[Patent Literature 66]
Japanese Patent Application Publication, Tokukaihei, No. 1-318021 (1989)
[Patent Literature 67]
Specification of European Patent No. 1521601
[Patent Literature 68]
Japanese Patent Application Publication, Tokukai, No. 2007-284675
[Patent Literature 69]
Pamphlet of International Publication No. WO 2011/078298
[Patent Literature 70]
Pamphlet of International Publication No. WO 2010/095427
[Patent Literature 71]
Pamphlet of International Publication No. WO 2011/126079
[Patent Literature 72]
Specification of U.S. Patent Application Publication No. 2011/0112252
[Patent Literature 73]
Specification of European Patent No. 0819721
[Patent Literature 74]
Japanese Patent Application Publication, Tokukai, No. 2003-238696

Non-Patent Literature

[Non-patent Literature 1]
Modern Superabsorbent Polymer Technology (1998) (in particular, p. 39-44, p. 97-103, p. 197-199, etc.)

SUMMARY OF INVENTION

Technical Problem

An object of the present invention is to provide (i) a polyacrylic acid (salt)-based water-absorbing agent which is less likely to cause gel blocking and is suitable for a sanitary product and an absorbent article each being thin and containing a large amount of a water-absorbing agent, and which, while maintaining or hardly losing the other physical properties (a fluid retention capacity and a bulk specific gravity) of the water-absorbing agent, simultaneously achieves a high water absorbing speed (e.g., FSR), a high fluid retention capacity under load, high liquid permeability, and salt tolerance, and (ii) a method for producing the polyacrylic acid (salt)-based water-absorbing agent.

Solution to Problem

Inventors of the present invention, who had carried out diligent study so as to attain the object, found that how a surface-crosslinked layer is formed greatly affects simultaneous achievement of a high water absorbing speed, a high fluid retention capacity under load, high liquid permeability, and salt tolerance. Specifically, the inventors of the present invention found that uniform formation of a strong (thick) crosslinked layer on a surface of a water-absorbing resin powder makes it possible to obtain a water-absorbing agent which has a high water absorbing speed, a high fluid retention capacity under load, high liquid permeability, and salt tolerance.

Then, the inventors of the present invention accomplished the present invention by finding that a water-absorbing agent of the present invention can be stably obtained in a case where in a surface crosslinking step, which is one of steps of a process for producing a polyacrylic acid (salt)-based water-absorbing agent, a mixture containing water, a surface crosslinking agent, and a water-absorbing resin powder is subjected to a heat treatment under a condition that a surface crosslinking agent C2 compound and/or a surface crosslinking agent C3 compound have/has a gas density of not less than 0.01 g/L.

Specifically, a polyacrylic acid (salt)-based water-absorbing agent of the present invention, whose surface and its vicinity are crosslinked by an organic surface crosslinking agent, characterized by satisfying the following (A)-(D):

(A) Free Swell Rate (FSR) of at least 0.28 g/g/s, or Absorption Time (Vortex) of 42 seconds or less;
(B) Absorption Against Pressure (AAP) of at least 20 g/g;
(C) Salt Tolerance Index represented by the following Formula 1 satisfying the following Formula 2:

$$\text{Salt Tolerance Index} = (CRCdw)/(CRCs) \qquad \text{(Formula 1)}$$

where CRCdw is a centrifuge retention capacity (unit; g/g) for deionized water (dw), and
CRCs is a centrifuge retention capacity (unit; g/g) for a 0.9 weight % saline, $$\text{Salt Tolerance Index} \geq 0.49 \times CRCs - 7.47 \qquad \text{(Formula 2);}$$

and
(D) Bulk Specific Gravity of 0.55 to 0.70 g/cm$^3$.

A method for producing a polyacrylic acid (salt)-based water-absorbing agent of the present invention, includes heat treating a mixture containing water, a surface crosslinking agent and a water-absorbing resin powder, wherein the water-absorbing resin powder is heat treated for at least five minutes from a start of raising a temperature with a gas density of a surface crosslinking agent C2 compound and/or a surface crosslinking agent C3 compound being at least 0.01 g/L.

Where the surface crosslinking agent C2 compound is a compound, of which longest carbon chain has 2 carbons, containing a total number of carbons of 3 or less, with either one of an oxygen atom or a nitrogen atom being bonded to each of carbon atoms at both ends of the carbon chain; and the surface crosslinking agent C3 compound is a compound, of which longest carbon chain has 3 carbons, containing a total number of carbons of 4 or less, with either one of an oxygen atom or a nitrogen atom being bonded to each of different carbon atoms on the carbon chain; and the gas density is a weight of the surface crosslinking agent C2 compound or the surface crosslinking agent C3 compound that is contained per unit volume of a non-condensable gas.

Advantageous Effects of Invention

A method for producing a polyacrylic acid (salt)-based water-absorbing agent in accordance with the present invention makes it possible to (i) uniformly form a strong crosslinked layer on a surface of a water-absorbing resin powder and (ii) obtain a water-absorbing agent which simultaneously achieves a high water absorbing speed, a high fluid retention capacity under load, high liquid permeability, and salt tolerance. Further, the polyacrylic acid (salt)-based water-absorbing agent in accordance with the present invention causes no reduction in fluid retention capacity and bulk specific gravity, and is preferably used in sanitary products such as disposable diapers, sanitary napkins, and incontinence pads.

BRIEF DESCRIPTION OF DRAWINGS

The FIGURE has graphs in which (i) amounts of decrease in fluid retention capacity caused by surface crosslinking when a surface crosslinking time is changed and (ii) residual ratios of a surface crosslinking agent are plotted in Example 2 and Comparative Example 2.

DESCRIPTION OF EMBODIMENTS

Hereinafter, a polyacrylic acid (salt)-based water-absorbing agent in accordance with the present invention and a method for producing the polyacrylic acid (salt)-based water-absorbing agent will be described in detail. It should be noted that the scope of the present invention is not limited to the description and can be embodied with modifications other than the following exemplary embodiments but not departing from the gist of the present invention. More specifically, the present invention shall not be construed as being limited to the following embodiments, may be modified in many ways within the scope of common general technical knowledge of a person skilled in the art. The technical scope of the present invention can encompass any modifications obtainable by appropriately combining technical means disclosed in different embodiments.

[1] Definitions of Terms (1-1) "Water-Absorbing Resin", "Water-Absorbing Resin Powder", "Water-Absorbing Resin Particles", and "Water-Absorbing Agent"

The term "water-absorbing resin" as used in the present invention means a water-swelling and water-insoluble polymer gelatinizer that satisfies the following physical properties. Specifically, the term "water-absorbing resin" as used in the present invention means a polymer gelatinizer that satisfies (i) CRC (fluid retention capacity without load) defined as "water-swelling" in ERT442.2-02 and having 5 g/g or higher and (ii) Ext (water soluble component) defined as "water-insoluble" in ERT470.2-02 and having not more than 50 weight %.

The water-absorbing resin can be designed according to its purpose of use and its object, and is not limited to a particular water-absorbing resin. The water-absorbing resin is preferably a hydrophilic crosslinked polymer which has been obtained by crosslinking and polymerizing unsaturated monomers each of which has a carboxyl group. Moreover, the water-absorbing resin does not need to be in a form in which the water-absorbing resin is wholly a crosslinked polymer, and can be a water-absorbing resin composition that contains, for example, an additive to the extent that the physical properties (CRC and Ext) mentioned above are satisfied.

The "water-absorbing resin" may refer to not only a pre-shipment end product but also an intermediate produced during a process for producing the water-absorbing resin (e.g., a hydrogel-forming crosslinked polymer after polymerization, a dried polymer after drying, a pulverized polymer after pulverization, a water-absorbing resin powder before surface crosslinking, or the like), and all of these are collectively referred to as the "water-absorbing resin".

In order to make it clear that water-absorbing resins that are in respective specific states are in the respective specific states, the present invention uses the wordings below to distinguish those water-absorbing resins. Specifically, the present invention refers to (i) a water-absorbing resin before surface crosslinking as a "water-absorbing resin powder", (ii) a water-absorbing resin after surface crosslinking as "water-absorbing resin particles", and (iii) a water-absorbing resin that serves as an end product as a "water-absorbing agent".

More specifically, the term "water-absorbing resin powder" as used in the present invention means a particulate water-absorbing resin to be obtained by polymerization, gel grinding (optional), drying, pulverization (optional), and classification and blending (depending on circumstances), which are steps of a production process. Further, the term "water-absorbing resin particles" as used in the present invention means a water-absorbing resin to be obtained by surface-crosslinking the water-absorbing resin powder. That is, the "water-absorbing resin powder" and the "water-absorbing resin particles" are distinguished from each other in accordance with whether or not surface crosslinking is carried out.

Further, the term "water-absorbing agent" as used in the present invention means a water-absorbing resin as an end product which contains, in an amount preferably of not less than 70 weight % and more preferably of not less than 85 weight %, a water-absorbing resin obtained by adding various additives (e.g., a liquid permeability improving agent) to the water-absorbing resin particles.

In addition, the present invention also refers to, as a "water-absorbing agent", a composition containing a chelating agent, a reducing agent, an antioxidant, an anti-coloring agent, and the like each in an amount preferably of 0 weight % to 10 weight % and more preferably of 0.1 weight % to 1 weight % based on the "water-absorbing agent".

A "water-absorbing resin" of the present invention is not particularly limited in form, and it is possible to select a water-absorbing resin in any form such as a sheet form, a fiber form, a film form, a particulate form, a gel form, or a powdery form. From the viewpoint of a particle size and a moisture content of a water-absorbing agent to be obtained, it is preferable to select, as the "water-absorbing resin" of the present invention, a particulate water-absorbing resin.

(1-2) "Polyacrylic Acid (Salt)"

The term "polyacrylic acid (salt)" as used in the present invention refers to polyacrylic acid and/or a salt thereof, and means a polymer that contains, as a main component, a repeating unit of acrylic acid and/or a salt thereof (hereinafter referred to as "acrylic acid (salt)") and that contains a graft component as an optional component.

The term "main component" means that the acrylic acid (salt) is contained (used) in an amount normally of 50 mol % to 100 mol %, preferably of 70 mol % to 100 mol %, more preferably of 90 mol % to 100 mol %, and especially even more preferably of substantially 100 mol %, based on a total amount of monomers for use in polymerization (excluding an internal crosslinking agent).

(1-3) "EDANA" and "ERT"

The term "EDANA" is an abbreviation for European Disposables and Nonwovens Associations. The term "ERT" is an abbreviation for EDANA Recommended Test Methods, which is an European standard method for measuring a water-absorbing resin. In the present invention, physical properties of a water-absorbing resin are measured in conformity with the ERT master copy (publicly known literature, revised in 2002) unless otherwise specified.

(a) "CRC" (ERT 441.2-02)

The term "CRC" is an abbreviation for "Centrifuge Retention Capacity" and refers to a fluid retention capacity without load (hereinafter also referred to as a "fluid retention capacity") of a water-absorbing resin.

Specifically, the CRC refers to a fluid retention capacity (unit; g/g) measured after 0.200 g of a water-absorbing resin contained in a nonwoven fabric bag is immersed in a large excess of a 0.9 weight % aqueous sodium chloride solution (physiological saline) for 30 minutes so as to be allowed to freely swell, and then the water-absorbing resin is drained in a centrifuge (250 G).

(b) "AAP" (ERT 442.2-02)

The term "AAP" is an abbreviation for "Absorption Against Pressure" and refers to a fluid retention capacity under load of a water-absorbing resin.

Specifically, the AAP refers to a fluid retention capacity (unit; g/g) measured after 0.900 g of a water-absorbing resin is allowed to swell in a large excess of a 0.9 weight % aqueous sodium chloride solution (physiological saline) for one hour under a load of 2.06 kPa (21 g/cm$^3$, 0.3 psi). Alternatively, the AAP may be measured by replacing the above load with a load of 4.83 kPa (49 g/cm$^2$, 0.7 psi).

(c) "Ext" (ERT 470.2-02)

The term "Ext" is an abbreviation for "Extractables" and refers to a water soluble component (water soluble component amount) of a water-absorbing resin.

Specifically, the Ext refers to a dissolved polymer amount (unit; weight %) obtained by adding 1.0 g of a water-absorbing resin to 200 ml of a 0.9 weight % aqueous sodium chloride solution and stirring a resultant mixture at 500 rpm for 16 hours. Note that the dissolved polymer amount is measured by pH titration.

(d) "PSD" (ERT420.2-02)

The term "PSD" is an abbreviation for "Particle Size Distribution" and refers to a particle size distribution of a water-absorbing resin which particle size distribution is measured by sieve classification.

Note that a weight average particle diameter (D50) and a logarithmic standard deviation (σζ) of a particle size distribution are measured according to a method similar to "(3) Mass-Average Particle Diameter (D50) and Logarithmic Standard Deviation (σζ) of Particle Diameter Distribution", which is a method disclosed in the specification of U.S. Pat. No. 7,638,570.

(e) Other physical properties of water-absorbing resin defined by EDANA

The term "Residual Monomers" (ERT410.2-02) refers to amounts of monomers left in a water-absorbing resin.

The term "Moisture Content" (ERT430.2-02) refers to a moisture content of a water-absorbing resin.

The term "Density" (ERT460.2-02) refers to a bulk specific gravity of a water-absorbing resin. Note that in the present invention, the bulk specific gravity is measured in conformity with JIS K 3362 with reference to ERT460.2-02.

(1-4) "Liquid Permeability"

The term "Liquid permeability" as used in the present invention refers to flowability a liquid passing through a space between respective particles of a swollen gel under load or without load. The "liquid permeability" is measured typically as a Saline Flow Conductivity (SFC) or Gel Bed Permeability (GBP).

The term "SFC" refers to liquid permeability of a 0.69 weight % aqueous sodium chloride solution based on 0.9 g of a water-absorbing resin under a load of 2.06 kPa, and is measured according to the SFC test method disclosed in the specification of U.S. Pat. No. 5,669,894.

The term "GBP" refers to liquid permeability of a 0.9 weight % aqueous sodium chloride solution based on a water-absorbing resin which is under load (0.3 psi) or is allowed to freely swell, and is measured according to the GBP test method disclosed in the pamphlet of the International Publication No. WO 2005/016393.

(1-5) "FSR (Free Swell Rate)" and "Vortex (Absorption Time)"

"FSR (Free Swell Rate)" and "Vortex (Absorption Time)" as used in the present invention are each an index indicative of water absorbing ability of a water-absorbing resin. "FSR (Free Swell Rate)" refers to a fluid retention capacity (unit; g/g/s) per unit time, and "Vortex (Absorption Time)" refers to a time (unit; second) required for a predetermined amount of water-based liquid to be absorbed. Note that it is described later in Examples how to specifically measure "FSR (Free Swell Rate)" and "Vortex (Absorption Time)". Note also that the term "FSR" is an abbreviation for "Free Swell Rate".

(1-6) "Salt Tolerance Index"

The term "Salt Tolerance Index" as used in the present invention is an index defined based on Formula 1 below, and is a parameter indicative of a degree of decrease in centrifuge retention capacity caused by an increase in salt concentration. Thus, in a case where the "Salt Tolerance Index" has a smaller value, a decrease in centrifuge retention capacity caused by an increase in salt concentration is made smaller. This means that a higher salt tolerance is achieved.

$$\text{Salt Tolerance Index} = (CRCdw)/(CRCs) \quad \text{(Formula 1)}$$

where CRCdw is a centrifuge retention capacity (g/g) for deionized water (dw), and CRCs is a centrifuge retention capacity (g/g) for a 0.9 weight % saline.

(1-7) Others

In this specification, a range "X to Y" refers to "not less than X and not more than Y". Moreover, unless otherwise specified, "t (ton)", which is a unit of weight, refers to "metric ton", and "ppm" refers to "ppm by weight". Further, " . . . acid (salt)" refers to " . . . acid and/or salt thereof", and "(meth)acrylic" means "acrylic and/or methacrylic".

[2] A Method for Producing Polyacrylic Acid (Salt)-Based Water-Absorbing Agent (2-1) Step of Preparing Acrylic Acid (Salt)-Based Aqueous Monomer Solution In this specification, the term "acrylic acid (salt)-based aqueous monomer solution" refers to an aqueous solution of monomers (hereinafter also referred to as an "aqueous monomer solution") which aqueous solution contains acrylic acid (salt) as a main component. The acrylic acid (salt)-based aqueous monomer solution appropriately contains constituent components of a water-absorbing resin powder, such as crosslinking agent(s), graft component(s), and minute component(s) (such as a chelating agent, a surfactant, and a dispersing agent). The acrylic acid (salt)-based aqueous monomer solution is subjected to polymerization as it is with a polymerization initiator added thereto.

The acrylic acid (salt) can be unneutralized, partially neutralized, fully neutralized, or excessively neutralized. The acrylic acid (salt)-based aqueous monomer solution, which is not limited in form of solution, can be a slurry aqueous solution (aqueous dispersion solution). Note, however, from the viewpoint of physical properties of a water-absorbing agent to be obtained, the acrylic acid (salt)-based aqueous monomer solution is preferably in a form of an aqueous solution containing an acrylic acid (salt)-based monomer whose concentration is not more than a saturating concentration.

A solvent contained in the aqueous monomer solution does not need to be 100 weight % water but can contain a water-soluble organic solvent (e.g., alcohol or the like) in an amount preferably of 0 weight % to 30 weight % and more preferably of 0 weight % to 5 weight %.

In this specification, the term "acrylic acid (salt)-based aqueous monomer solution under preparation" refers to an aqueous solution of acrylic acid (salt), which aqueous solution is to be prepared as an aqueous monomer solution whose main component is acrylic acid (salt), but to which aqueous solution not all constituent components have been added. Specific examples of the acrylic acid (salt)-based aqueous monomer solution under preparation encompass an aqueous acrylic acid solution and an aqueous fully or partially neutralized acrylic acid salt solution.

In a case where the acrylic acid (salt)-based aqueous monomer solution under preparation is further neutralized, mixed with water serving as a solvent, or mixed with the minute component(s), a final acrylic acid (salt)-based aqueous monomer solution is obtained. Note that the final acrylic acid (salt)-based aqueous monomer solution, which has not been or has been introduced into a polymerizer and has not started to be polymerized, is referred to as an "acrylic acid (salt)-based aqueous monomer solution which has been prepared and unpolymerized".

(Monomer)

The acrylic acid (salt)-based monomer is not particularly limited provided that the acrylic acid (salt)-based monomer is made into a water-absorbing resin by polymerization. Examples the acrylic acid (salt)-based monomer encompass: anionic unsaturated monomers and salts thereof such as (meth)acrylic acid, (anhydrous) maleic acid, itaconic acid, cinnamic acid, vinyl sulfonic acid, allyltoluene sulfonic acid, vinyltoluene sulfonic acid, styrene sulfonic acid, 2-(meth)acrylamide-2-methylpropane sulfonic acid, 2-(meth)acryloyl ethane sulfonic acid, 2-(meth)acryloyl propane sulfonic acid, and 2-hydroxyethyl(meth)acryloyl phosphate; mercapto group-containing unsaturated monomers; phenolic hydroxide group-containing unsaturated monomers; amide group-containing unsaturated monomers such as (meth)acrylamide, N-ethyl(meth)acrylamide, and N,N-dimethyl(meth)acrylamide; amino group-containing unsaturated monomers such as N,N-dimethylaminoethyl(meth)acrylate, N,N-dimethylaminopropyl(meth)acrylate, and N,N-dimethylaminopropyl(meth)acrylamide; and other monomers.

The acrylic acid (salt)-based monomer is contained in an amount normally of not less than 50 mol %, preferably of not less than 70 mol %, more preferably of not less than 80 mol %, even more preferably of not less than 90 mol %, and especially even more preferably of not less than 95 mol % (an upper limit is 100 mol %), based on a total amount of monomer(s) contained in the acrylic acid (salt)-based aqueous monomer solution and excluding an internal crosslinking agent.

A neutralization rate of the acrylic acid (salt)-based monomer or the hydrogel-forming crosslinked polymer after polymerization in accordance with the present invention is not limited to a particular neutralization rate. From the viewpoint of physical properties of a water-absorbing agent to be obtained or reactivity of a surface crosslinking agent, the neutralization rate ranges preferably from 40 mol % to 90 mol %, more preferably from 50 mol % to 80 mol %, and even more preferably from 60 mol % to 74 mol %.

The neutralization rate preferably falls within the above range for the reasons below. A low neutralization rate tends to lower a water absorbing speed of a water-absorbing agent to be obtained, whereas a high neutralization rate tends to lower reactivity of a water-absorbing resin powder with a surface crosslinking agent, particularly with a dehydration reactive surface crosslinking agent (described later), so that a water-absorbing agent tends to be less productive or have lower liquid permeability (e.g., SFC) and a lower fluid retention capacity under load (e.g., AAP or PUP).

The acrylic acid (salt)-based monomer or the hydrogel-forming crosslinked polymer can be partially or totally salt from the viewpoint of the fluid retention capacity without load (CRC) and the fluid retention capacity under load (AAP or PUP) of a water-absorbing agent to be obtained as an end product. The acrylic acid (salt)-based monomer or the hydrogel-forming crosslinked polymer is preferably a monovalent salt such as alkali metal salt (sodium salt, lithium salt, or potassium salt), ammonium salt, or an amine. Of these monovalent salts, alkali metal salt is more preferable, sodium salt and/or potassium salt are/is even more preferable, and sodium salt is particularly preferable from the viewpoint of cost and physical properties.

(Polymerization Inhibitor)

The acrylic acid (salt)-based monomer of the present invention contains a polymerization inhibitor. The polymerization inhibitor is exemplified by but not particularly limited to N-oxyl compounds, manganese compounds, and substituted phenol compounds, each of which is disclosed in the pamphlet of International Publication No. WO 2008/096713, and other compounds. Of these polymerization inhibitors, the substituted phenol compounds are preferable. Of the substituted phenol compounds, methoxyphenols are particularly preferable.

Examples of the methoxyphenols encompass o-, m-, p-methoxyphenol, methoxyphenols each having one or more substituents such as a methyl group, a t-butyl group, and a hydroxyl group, and the like. In the present invention, p-methoxyphenol is particularly preferable.

The polymerization inhibitor is contained in the acrylic acid (salt)-based monomer in an amount preferably of 5 ppm to 200 ppm, more preferably of 5 ppm to 160 ppm, 10 ppm to 160 ppm, 10 ppm to 100 ppm, and 10 ppm to 80 ppm in this order, and most preferably of 10 ppm to 70 ppm, based on a total amount of the acrylic acid (salt)-based monomer. The polymerization inhibitor which is contained in an amount of more than 200 ppm may cause a deterioration in color tone (coloring such as yellowing or yellow color change) in a water-absorbing agent to be obtained. Meanwhile, the polymerization inhibitor which is contained in an amount of less than 5 ppm, i.e., the polymerization inhibitor which is removed by refining such as distillation may increase a risk of causing unintended polymerization.

(Internal Crosslinking Agent)

In the present invention, an internal crosslinking agent is appropriately used in polymerization. The internal crosslinking agent is not particularly limited and can be a publicly known internal crosslinking agent. Examples of the internal crosslinking agent encompass N,N'-methylenebis(meth)acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethyleneoxide modified trimethylol propane tri(meth)acrylate, pentaerythritol hexa(meth)acrylate, triallyl cyanurate, triallyl isocyanurate, triallyl phosphate, triallylamine, poly(meth)allyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth) acrylate, and the like. Of these internal crosslinking agents, one or more kinds of internal crosslinking agents can be used in consideration of reactivity. In particular, it is preferable to use a compound having two or more polymerizable unsaturated groups.

Further, in a case where two or more internal crosslinking agents are used in combination, an internally crosslinked structure can be changed by changing reactivity of functional groups of the internal crosslinking agents. Thus, it is preferable that internal crosslinking agents having different functional groups be selected for use in combination from amide compounds, (meth)acrylate compounds, allylic compounds, amine compounds, imine compounds, alcohol compounds, carbonate compounds, and glycidyl compounds.

A used amount of the internal crosslinking agent can be appropriately determined in accordance with desired physical properties of the water-absorbing agent. The used amount of the internal crosslinking agent ranges preferably from 0.001 mol % to 5 mol %, more preferably from 0.005 mol % to 2 mol %, and even more preferably from 0.01 mol % to 1 mol %, based on a total amount of the acrylic acid (salt)-based monomer. In a case where two or more internal crosslinking agents are used in combination, a used amount of each of the internal crosslinking agents ranges preferably from 0.001 mol % to 5 mol %, more preferably from 0.005 mol % to 2 mol %, and even more preferably from 0.01 mol % to 1 mol %, based on the total amount of the acrylic acid (salt)-based monomer.

In a case where the used amount of the internal crosslinking agent (or a total amount of the two or more internal crosslinking agents used in combination) is less than 0.001 mol %, a water-absorbing agent to be obtained increases in water soluble component and consequently may be insufficient in amount of water absorption under load. Meanwhile, in a case where the used amount of the internal crosslinking agent is more than 5 mol %, a water-absorbing agent to be obtained increases in internal crosslink density and consequently may be insufficient in amount of water absorption. Note that all of the internal crosslinking agent(s) can be added to the acrylic acid (salt)-based aqueous monomer solution which has been prepared and unpolymerized, or a part of the internal crosslinking agent(s) can be added to the acrylic acid (salt)-based aqueous monomer solution which has started to be polymerized.

(Dispersing Agent)

A dispersing agent that can be used in the present invention is not particularly limited. The dispersing agent is preferably a water absorbent polymer dispersing agent, a water absorbent hydrophilic polymer dispersing agent, or a water-soluble polymer dispersing agent, and more preferably a water-soluble polymer dispersing agent. A weight average molecular weight of the dispersing agent is appropriately determined according to a type of the dispersing agent. The weight average molecular weight of the dispersing agent ranges preferably from 500 to 10,000,000, more preferably from 5,000 to 5,000,000, and especially even more preferably from 10,000 to 3,000,000.

The dispersing agent is not particularly limited in type. Examples of the dispersing agent encompass hydrophilic polymers such as starch, a starch derivative, cellulose, a cellulose derivative, polyvinyl alcohol (PVA), carboxymethyl cellulose (sodium), hydroxyethyl cellulose, polyacrylic acid (salt), crosslinked polyacrylic acid (salt), and the like. Of these dispersing agents, a water-soluble polymer dispersing agent selected from starch, cellulose, and PVA is preferable from the viewpoint of not impairing hydrophilicity of the water-absorbing agent of the present invention.

A used amount of the dispersing agent ranges preferably from 0 part by weight to 50 parts by weight, more preferably from 0.01 parts by weight to 20 parts by weight, even more preferably from 0.05 parts by weight to 10 parts by weight, and especially even more preferably from 0.1 parts by weight to 5 parts by weight, based on 100 parts by weight of the acrylic acid (salt)-based monomer. The dispersing agent which is used in an amount of more than 50 parts by weight may cause a deterioration in water absorbent property of the water-absorbing agent.

(2-2) Polymerization Step (Polymerization Method)

A polymerization method for obtaining a water-absorbing agent of the present invention is exemplified by spray polymerization, droplet polymerization, bulk polymerization, precipitation polymerization, aqueous solution polymerization, reverse phase suspension polymerization, and the like. In order to attain the object of the present invention, it is preferable to employ, as the polymerization method, aqueous solution polymerization or reverse phase suspension polymerization, each of which is carried out by use of an aqueous solution of monomers.

The aqueous solution polymerization is a method for polymerizing an aqueous monomer solution without using a dispersion solvent. The aqueous solution polymerization is exemplified by polymerization methods disclosed in the specifications of, for example, U.S. Pat. Nos. 4,625,001, 4,873,299, 4,286,082, 4,973,632, 4,985,518, 5,124,416, 5,250,640, 5,264,495, 5,145,906, 5,380,808, European Patent No. 0811636, European Patent No. 0955086, and European Patent No. 0922717.

The reverse phase suspension polymerization is a method for polymerizing an aqueous monomer solution by suspending the aqueous monomer solution in a hydrophobic organic solvent, and does not particularly require a pulverization step and a classification step. The reverse phase suspension polymerization is exemplified by polymerization methods disclosed in the specifications of, for example, U.S. Pat. Nos. 4,093,776, 4,367,323, 4,446,261, 4,683,274, and 5,244,735. Monomers, polymerization initiators, etc. disclosed in these patent literatures are applicable to the reverse phase suspension polymerization in the present invention.

The spray polymerization or the droplet polymerization is a method for polymerizing an aqueous monomer solution by spraying or dropping the aqueous monomer solution in a gas phase, and does not particularly require a pulverization step and a classification step. The spray polymerization or the droplet polymerization is exemplified by polymerization methods disclosed in the pamphlets of, for example, International Publication No. WO 2008/095892, International Publication No. 2008/095893, International Publication No. WO 2008/095901, International Publication No. WO 2009/027356, International Publication No. WO 2010/003855, and International Publication No. WO 2010/003897. Monomers, polymerization initiators, etc. disclosed in these patent literatures are applicable to the spray polymerization or the droplet polymerization in the present invention.

A concentration of the aqueous monomer solution during the polymerization is not particularly limited. The concentration ranges preferably from 20 weight % to a saturating concentration, more preferably from 25 weight % to 80 weight %, and even more preferably from 30 weight % to 70 weight %. The aqueous monomer solution which has a concentration of less than 20 weight % may reduce productivity of a water-absorbing agent to be obtained.

Note that since the polymerization which is carried out by use of a monomer slurry (aqueous dispersion of acrylate) causes a deterioration in physical property of a water-absorbing agent to be obtained, it is preferable to carry out the polymerization by use of the aqueous monomer solution whose concentration is not more than the saturating concentration (see Japanese Patent Application Publication, Tokukaihei, No. 1-318021).

In order to improve physical properties of a water-absorbing agent by promoting the polymerization, it is possible to appropriately carry out, during the polymerization, the step of degassing dissolved oxygen (e.g., the step of replacing the dissolved oxygen with inert gas). In addition, for the purpose of, for example, increasing a water absorbing speed of a water-absorbing agent, increasing a surface area of the water-absorbing agent, or increasing a drying speed of the water-absorbing agent, by causing the aqueous monomer solution to contain air bubbles (particularly inert gas) or various kinds of foaming agents (e.g., an organic or inorganic carbonate, an azo compound, and a urea compound) during the polymerization, it is possible for the aqueous monomer solution to form foams so that a volume of the aqueous monomer solution or a hydrogel to be obtained is increased by, for example, 1.001 times to 10 times during the polymerization or during the drying.

The polymerization step in the present invention can be carried out under any of a normal atmospheric pressure, a reduced pressure, and an increased pressure. The polymerization step is preferably carried out under the normal atmospheric pressure (101.3 kPa (1 atmospheric pressure)) or under an atmospheric pressure close to the normal atmospheric pressure (normal atmospheric pressure ±10%). A temperature at which polymerization is started ranges preferably from 15 to 130° C. and more preferably from 20 to 120° C., though depending on a type of a polymerization initiator to be used.

(Polymerization Initiator)

A polymerization initiator used in the present invention is appropriately selected in accordance with a form of polymerization, and is not particularly limited. Examples of the polymerization initiator encompass a photodegradable polymerization initiator, a pyrolytic polymerization initiator, a redox polymerization initiator, and the like. The polymerization in the present invention is initiated by use of any of these polymerization initiators.

Examples of the photodegradable polymerization initiator encompass a benzoin derivative, a benzyl derivative, an acetophenone derivative, a benzophenone derivative, an azo compound, and the like.

Examples of the pyrolytic polymerization initiator encompass: persulfates such as sodium persulfate, potassium persulfate, and ammonium persulfate; peroxides such as hydrogen peroxide, t-butyl peroxide, and methylethylketone peroxide; azo compounds such as 2,2'-azobis(2-amidinopropane)dihydrochloride and 2,2'-azobis[2-(2-imidazoline-2-yl)propane]dihydrochloride; and the like.

Examples of the redox polymerization initiator encompass systems in each of which a reducing compound such as L-ascorbic acid or sodium hydrogen sulfite is used in combination with any of the persulfates or any of the peroxides.

Further, it is also a preferable aspect to use the photodegradable polymerization initiator and the pyrolytic polymerization initiator in combination. Still further, active energy lines such as an ultraviolet ray, an electron ray, and a gamma ray can be used alone or used in combination with the polymerization initiator.

A used amount of the polymerization initiator ranges preferably from 0.0001 mol % to 1 mol % and more preferably from 0.0005 mol % to 0.5 mol % based on a total amount of the monomer(s). The polymerization initiator which is used in an amount of more than 1 mol % may cause a deterioration in color tone of a water-absorbing agent. Meanwhile, the polymerization initiator which is used in an amount of less than 0.0001 mol % may cause an increase in residual monomer.

(More Suitable Polymerization Method)

As a method for polymerizing an acrylic acid (salt)-based aqueous monomer solution in the present invention, at least one of reverse phase suspension polymerization, spray polymerization, droplet polymerization, and aqueous solution polymerization, particularly the aqueous solution polymerization, is employed from the viewpoint of, for example, physical properties (e.g., water absorbing speed and liquid permeability) of a water-absorbing agent and ease of control of polymerization.

Examples of a preferable aspect of the aqueous solution polymerization encompass (i) high-temperature starting aqueous solution polymerization in which a polymerization starting temperature is preferably not lower than 40° C., more preferably not lower than 50° C., even more preferably not lower than 60° C., especially even more preferably not lower than 70° C., and most preferably not lower than 80° C. (an upper limit is a boiling point), (ii) high-concentration aqueous solution polymerization in which a monomer concentration is preferably not less than 40 weight %, more preferably not less than 45 weight %, and even more preferably not less than 50 weight % (an upper limit is not more than 90 weight %, preferably not more than 80 weight %, and more preferably not more than 70 weight %), and (iii) high-concentration and high-temperature starting aqueous solution polymerization which is a combination of the high-temperature starting aqueous solution polymerization and the high-concentration aqueous solution polymerization.

A preferable form of polymerization is kneader polymerization or belt polymerization. Examples of a preferable form of the aqueous solution polymerization encompass continuous belt polymerization (disclosed in the specifications of, for example, U.S. Pat. Nos. 4,893,999, 6,241,928, U.S. Patent Application Publication No. 2005/215734, and International Publication No. WO 2008/114847), continuous kneader polymerization, batch kneader polymerization (disclosed in the specifications of, for example, U.S. Pat. Nos. 6,987,151, 6,710,141, and International Publication No. WO 2008/114848), and the like.

The polymerization method can also be exemplified by high-temperature starting continuous aqueous solution polymerization, high-concentration continuous aqueous solution polymerization, and high-concentration and high-temperature starting continuous aqueous solution polymerization, each of which is a combination of the preferable aspect (described earlier) and the preferable form of polymerization (described earlier).

Another preferable example of the polymerization method can be exemplified by batch polymerization or continuous kneader polymerization in which a polymerization starting temperature is preferably not lower than 15° C. and a monomer concentration is not less than 30 weight %.

Moreover, in carrying out the polymerization, a polymerization starting time (a time between the addition of the polymerization initiator and the start of polymerization) is preferably longer than 0 second and not longer than 300 seconds, and more preferably 1 to 240 seconds.

By employing the aqueous solution polymerization described earlier, it is possible to produce a water-absorbing resin with high productivity. Note that such a polymerization method as described earlier is preferably employed in a huge-scale production apparatus whose production amount per line is large. The production amount is preferably not less than 0.5 t/hr, more preferably not less than 1 t/hr, even more preferably not less than 5 t/hr, and especially even more preferably not less than 10 t/hr.

(2-3) Gel Grinding Step

The present step is an optional step of obtaining a particulate hydrogel (hereinafter referred to as a "particulate hydrogel") by carrying out gel grinding with respect to a hydrogel-forming crosslinked polymer (hereinafter referred to as a "hydrogel") that is obtained through the polymerization step (particularly, aqueous solution polymerization).

In a case where the hydrogel is grain-refined by gel grinding, particularly gel grinding by mixing in aqueous solution polymerization, it is possible to achieve both water absorbing speed and liquid permeability of a water-absorbing agent to be obtained and further to improve impact resistance of the water-absorbing agent to be obtained. That is, in order to attain the object of the present invention, it is more preferable to employ aqueous solution polymerization than to employ reverse phase suspension polymerization in which gel grinding is not carried out. It is particularly preferable to employ aqueous solution polymerization in which gel grinding is carried out during polymerization (e.g., kneader polymerization) or after polymerization (e.g., belt polymerization, and kneader polymerization, if necessary).

A gel grinding device that can be used in the present invention is exemplified by but not particularly limited to a gel grinding device having a plurality of rotational stirring blades (e.g., a batch type or continuous double-armed kneader), a single-screwed extruder, a twin-screwed extruder, a meat chopper, and the like. Of these gel grinding devices, a screwed extruder having a porous plate at its end is preferable. The screwed extruder having a porous plate at its end is exemplified by a screwed extruder disclosed in Japanese Patent Application Publication, Tokukai, No. 2000-063527.

In the gel grinding step of the present invention, a hydrogel before gel grinding has a temperature (gel temperature) preferably of 60° C. to 120° C. and more preferably of 65° C. to 110° C. from the viewpoint of particle size control of a particulate hydrogel and physical properties of a water-absorbing agent. The hydrogel which has a gel temperature lower than 60° C. causes an increase in hardness of the hydrogel due to a characteristic of the hydrogel. This may make it difficult to control a particle shape and a particle size distribution during the gel grinding. Meanwhile, the hydrogel which has a gel temperature higher than 120° C. causes an increase in softness of the hydrogel. This may make it difficult to control the particle shape and the particle size distribution. Note that the above gel temperature can be controlled by, for example, a temperature during polymerization, or heating after the polymerization or cooling after the polymerization.

Further, a weight average particle diameter (D50) (defined by sieve classification) of a particulate hydrogel after gel grinding ranges preferably from 0.5 mm to 3 mm, more preferably from 0.6 mm to 2 mm, and even more preferably from 0.8 mm to 1.5 mm. Moreover, a ratio of a coarse particulate hydrogel having a particle diameter of not less than 5 mm is preferably not more than 10 weight %, more preferably not more than 5 weight %, and even more preferably not more than 1 weight %, with respect to a total amount of the particulate hydrogel.

In the present invention, the polymerization step and the gel grinding step can be carried out by any of the following methods: a kneader polymerization method of carrying out gel grinding with respect to a hydrogel-forming crosslinked polymer during polymerization; and a method of subjecting, to the gel grinding step, a hydrogel-forming crosslinked polymer obtained by continuous belt polymerization.

(2-4) Drying Step

The present step is a step of obtaining a dried polymer by drying a hydrogel obtained through, for example, the polymerization step. In a case where the aqueous solution polymerization is carried out in the polymerization step, a hydrogel is preferably subjected to gel grinding (grain refining) before being dried. Further, the dried polymer (an agglomerate) obtained by the present step can be supplied directly to subsequent step(s), which is/are the pulverization step and/or the classification step.

A drying method that can be employed in the present step is exemplified by but not particularly limited to various methods. Specific examples of the drying method encompass thermal drying, hot air drying, drying under reduced pressure, infrared drying, microwave drying, drying by azeotropic dehydration with a hydrophobic organic solvent, and high humidity drying by use of high temperature water vapor. These drying methods can be used solely or two of the drying methods can be used in combination. A drying temperature ranges preferably from 100 to 300° C. and more preferably from 150 to 250° C.

Further, a drying time, which depends on, for example, a surface area of the particulate hydrogel and a moisture content in the particulate hydrogel, and a type of a dryer, is not particularly limited. For example, the drying time ranges preferably from 1 minute to 5 hours and more preferably from 5 minutes to 1 hour. Further, a resin solid content calculated from a drying loss (change in weight of 1 g of a powder or particles before and after drying at 180° C. for 3 hours) is preferably not less than 80 weight %, more preferably 85 weight % to 99 weight %, and even more preferably 90 weight % to 98 weight %.

(2-5) Pulverization Step and/or Classification Step

The present step is a step of pulverizing and/or classifying the dried polymer obtained by the drying step and is preferably a step of obtaining a water-absorbing resin powder having a specific particle size. Note that the present step is different from (2-3) Gel grinding step (described earlier) in that a product to be pulverized has been subjected to the drying step. Further, a water-absorbing resin obtained after the pulverization step may be referred to as a "pulverized polymer".

(Particle Size Distribution)

A weight average particle diameter (D50) of a water-absorbing resin powder before surface crosslinking ranges preferably from 200 μm to 600 μm, more preferably from 200 μm to 550 μm, even more preferably from 250 μm to 500 μm, and especially even more preferably from 350 μm to 450 μm, from the viewpoint of, for example, water absorbing speed, liquid permeability, and fluid retention capacity under load of a water-absorbing agent to be obtained. Further, it is more favorable that a water-absorbing resin powder having a particle diameter of less than 150 μm defined by standard sieve classification (hereinafter referred to as a "fine powder") be contained in a smaller amount. An amount of the fine powder contained ranges preferably from 0 weight % to 5 weight %, more preferably from 0 weight % to 3 weight %, and even more preferably from 0 weight % to 1 weight %, from the viewpoint of, for example, liquid permeability of a water-absorbing agent to be obtained.

Still further, it is also more favorable that a water-absorbing resin powder having a particle diameter of not less than 850 μm, preferably of not less than 710 μm, defined by standard sieve classification (hereinafter referred to as "coarse particles") be contained in a smaller amount. An amount of the coarse particles contained ranges preferably from 0 weight % to 5 weight %, more preferably from 0 weight % to 3 weight %, and even more preferably from 0 weight % to 1 weight %, from the viewpoint of, for example, water absorbing speed of a water-absorbing agent to be obtained. Moreover, particles whose particle diameters are distributed in a range preferably of not less than 150 μm and less than 850 μm and more preferably of not less than 150 μm and less than 710 μm are contained in an amount preferably of not less than 95 weight %, more preferably of not less than 98 weight %, and even more preferably of not less than 99 weight % (an upper limit is 100 weight %), from the viewpoint of, for example, water absorbing speed, liquid permeability, and fluid retention capacity under load of a water-absorbing agent to be obtained.

The weight average particle diameter (D50) or the particle diameter (hereinafter also simply referred to as "particle size") of a water-absorbing resin powder can be controlled in the polymerization step, the gel grinding step, or the pulverization and/or the classification step after the drying step, and is preferably controlled particularly in the classification step after the drying step. Further, the particle size is measured by use of a JIS standard sieve (Z8801-1 (2000)) in accordance with the method defined in the specification of U.S. Pat. No. 7,638,570 or EDANA-ERT420.2-02.

The water-absorbing resin powder of the present invention can be in a form of spheres or an agglomerate of the spheres, or can be ground to have an uneven shape obtained through the pulverization step carried out with respect to the hydrogel or the dried polymer. From the viewpoint of water absorbing speed of a water-absorbing agent to be obtained, it is preferable that the water-absorbing resin powder be preferably ground to have an uneven shape or be an agglomerated material of the water-absorbing resin powder thus ground.

The particle size is also applied preferably to a particle size after surface crosslinking and more preferably to a particle size of a water-absorbing agent as an end product so that the object of the present invention is further attained. A small amount of a fine powder contained in a water-absorbing agent and having a particle size of less than 150 μm improves an SFC and thus is preferable.

(2-6) Fine Powder Recycling Step

A production method in accordance with the present invention preferably includes, after the drying step, the classification step (including a second classification step carried out after a surface crosslinking step; same applies to the following description) of separating a fine powder having passed through a standard sieve having a mesh size of 150 μm, and thereafter recycling (reusing), in a step carried out before the drying step, the fine powder or the fine powder to which water is added.

Note that the coarse particles removed in the classification step can be appropriately pulverized again. Moreover, the fine powder removed in the classification step can be disposed of, used for another purpose, or subjected to the present fine powder recycling step.

The present step allows a further increase in water absorbing speed of a water-absorbing agent to be obtained.

That is, in the production method in accordance with the present invention, the fine powder recycling step refers to a step of separating a fine powder (in particular, a fine powder containing, in an amount of not less than 70 weight %, particles having a particle diameter of less than 150 μm) generated in the drying step, and if necessary, in the pulverization step and/or the classification step, and thereafter before the drying step, preferably in the polymerization step, the gel grinding step, or the drying step, recycling the fine powder as it is, or recycling the fine powder by hydrating or granulating the fine powder.

Recycling of the fine powder allows control of particle sizes of a water-absorbing resin powder and a water-absorbing agent and allows a further increase in water absorbing speed of a water-absorbing resin to be obtained by the present step.

The fine powder to be recycled can be a fine powder before surface crosslinking or a fine powder after surface crosslinking. The fine powder is recycled in an amount preferably of 1 weight % to 40 weight % and more preferably of 5 weight % to 30 weight % based on the dried polymer.

A suitable fine powder recycling method of the present invention is a method in which the fine powder or a product obtained by hydrating or granulating the fine powder, and if necessary, an inorganic microparticle, for example is mixed in the aqueous monomer solution before polymerization, the hydrogel during polymerization, or a dryer used in the drying step. A method of recycling the fine powder in the aqueous monomer solution before polymerization is exemplified by the methods disclosed in the pamphlets of International Publications Nos. 92/001008 and 92/020723. A method of recycling the fine powder in the hydrogel during polymerization is exemplified by the methods disclosed in the pamphlets of International Publications Nos. 2007/074167, 2009/109563, 2009/153196, and 2010/006937. Further, a method of recycling the fine powder in the drying step (by use of a dryer) is exemplified by the method disclosed in the specification of, for example, U.S. Pat. No. 6,228,930. These fine powder recycling methods are suitably applicable to the fine powder recycling method of the present invention.

The above description has discussed a method for producing a water-absorbing resin powder that is a water-absorbing resin before surface crosslinking.

Further, the present invention makes it possible to obtain a water-absorbing agent that is provided with a high fluid retention capacity under load, high liquid permeability, and salt tolerance while maintaining a water absorbing speed (FSR) of at least 0.28 g/g/s of a water-absorbing resin powder. For example, the methods disclosed in Japanese Patent Application Publication, Tokukai, No. 2007-284675 and the pamphlets of International Publications Nos. WO 2011/078298, WO 2010/095427, and WO 2011/126079 are applicable to a specific method for producing a water-absorbing resin powder before surface crosslinking and has a water absorbing speed (FSR) of at least 0.28 g/g/s.

(2-7) Surface Crosslinking Agent Addition Step

The present step is a step of preparing a mixture containing a surface crosslinking agent to be subjected to the surface crosslinking step.

Surface crosslinking is commonly carried out by, for example, addition of an organic surface crosslinking agent (described later), polymerization of monomer(s) on a surface of a water-absorbing resin powder, or addition of a radical polymerization initiator such as persulfate and heating and/or ultraviolet irradiation. In a surface crosslinking agent addition step of the present invention, it is preferable to add the organic surface crosslinking agent to the water-absorbing resin powder obtained by the classification step (described earlier) and further to the water-absorbing resin obtained by the fine powder recycling step. Further, the surface crosslinking agent addition step can be carried out simultaneously with a liquid permeability improving agent addition step (described later).

(Organic Surface Crosslinking Agent)

An "organic surface crosslinking agent" as used in the present invention refers to an organic compound that can be surface-crosslinked with a water-absorbing resin by forming preferably a covalent bond or an ionic bond, more preferably a covalent bond with a functional group (in particular, a carboxyl group) of the water-absorbing resin. Specifically, the organic surface crosslinking agent is at least one kind of compound selected from a surface crosslinking agent C2 compound, a surface crosslinking agent C3 compound, and a surface crosslinking agent C4 compound, which are described later, and is more preferably a combination of two or more kinds of these compounds.

The surface crosslinking agent C2 compound is a compound, of which longest carbon chain has 2 carbons, containing a total number of carbons of 3 or less, with either one of an oxygen atom or a nitrogen atom being bonded to each of carbon atoms at both ends of the carbon chain. More preferably, a bond between the oxygen atom and a corresponding carbon atom and a bond between the nitrogen atom and a corresponding carbon atom are each a single bond. The surface crosslinking agent C2 compound has a molecular weight preferably of 120 or less, more preferably of 110 or less, even more preferably of 100 or less, and especially even more preferably of 90 or less.

Specific examples of the surface crosslinking agent C2 compound encompass ethylene glycol, ethanolamine, ethylenediamine, ethylene carbonate, 2-oxazolidinone, 3-amino-2-oxazolidinone, 2-imidazolidinone, ethyleneoxide, and the like. Of these surface crosslinking agent C2 compounds, ethylene glycol, ethanolamine, ethylenediamine, ethylene carbonate, 2-oxazolidinone, 2-imidazolidinone, or ethyleneoxide is more preferable, and ethylene carbonate, 2-oxazolidinone, 2-imidazolidinone, or ethyleneoxide is even more preferable.

The surface crosslinking agent C3 compound is a compound, of which longest carbon chain has 3 carbons, containing a total number of carbons of 4 or less, with either one of an oxygen atom or a nitrogen atom being bonded to each of at least two different carbon atoms on the carbon chain. More preferably, the number of the at least two different carbon atoms to each of which either one of the oxygen atom and the nitrogen atom is bonded is two. Even more preferably, a bond between the oxygen atom and a corresponding carbon atom and a bond between the nitrogen atom and a corresponding carbon atom are each a single bond. The surface crosslinking agent C3 compound has a molecular weight preferably of 120 or less, more preferably of 110 or less, and even more preferably of 105 or less.

Specific examples of the surface crosslinking agent C3 compound encompass 1,2-propanediol (also known as propylene glycol), 1,3-propanediol, 3-amino-1-propanol, 2-amino-1-propanol, 1-amino-2-propanol, propylene carbonate, 1,3-propanediyl carbonate, 4-methyl-2-oxazolidinone, 4-(hydroxymethyl)-2-oxazolidinone, glycerin carbonate, glycidol, glycerin, methyl glycerin, diethylene glycol, diethanol amine, and the like. Of these surface crosslinking agent C3 compounds, 1,2-propanediol, 1,3-propanediol, 3-amino-1-propanol, 2-amino-1-propanol, 1-amino-2-propanol, propylene carbonate, glycerin carbonate, glycidol, glycerin, methyl glycerin, diethylene glycol, or diethanol amine is more preferable, and 1,2-propanediol, 1,3-propanediol, propylene carbonate, glycerin carbonate, glycidol, glycerin, methyl glycerin, diethylene glycol, or diethanol amine is even more preferable.

The surface crosslinking agent C4 compound is a compound, of which longest carbon chain has 4 carbons, containing a total number of carbons of 5 or less, with either one of an oxygen atom or a nitrogen atom being bonded to each of at least two different carbon atoms on the carbon chain. More preferably, the number of the at least two different carbon atoms to each of which either one of the oxygen atom and the nitrogen atom is bonded is two. Even more preferably, a bond between the oxygen atom and a corresponding carbon atom and a bond between the nitrogen atom and a corresponding carbon atom are each a single bond. The surface crosslinking agent C4 compound has a molecular weight preferably of 120 or less, more preferably of 110 or less, and even more preferably of 105 or less.

Specific examples of the surface crosslinking agent C4 compound encompass: polyvalent alcohol compounds such as 1,4-butanediol and 1,3-butanediol; alkylene carbonate compounds such as butene carbonate; oxetane compounds; cyclic urea compounds such as a derivative of 2-imidazolidinone; and the like.

From the viewpoint of a more remarkable physical property of a water-absorbing agent to be obtained, an organic surface crosslinking agent containing a combination of a polyvalent alcohol and a compound different from the polyvalent alcohol is preferable. As the compound different from the polyvalent alcohol, an epoxy compound or an alkylene carbonate compound is preferable, and an alkylene carbonate compound is more preferable.

Further, it is also possible to use another surface crosslinking agent different from the organic surface crosslinking agent. The another surface crosslinking agent is preferably an organic compound or an inorganic compound and more preferably an organic compound. In addition, the another surface crosslinking agent is desirably an organic compound which (i) has, in a molecule, two or more functional groups that are capable of forming a covalent bond with a functional group of a water-absorbing resin, particularly a carboxyl group, and more preferably two or more functional groups that carry out a dehydration reaction with a carboxyl group, and (ii) has a molecular weight of 60 to 1000. Note that the another surface crosslinking agent which has, in a molecule, two or more functional groups that carry out the dehydration reaction is referred to as a dehydration reactive surface crosslinking agent in the present invention. Further, the another surface crosslinking agent desirably has solubility preferably of not less than 1 g, more preferably of not less than 5 g, and even more preferably of not less than 10 g, based on 100 g of water at 25° C.

The another surface crosslinking agent is preferably a surface crosslinking agent, of which longest carbon chain has at least 5 carbons. Specific examples of such a surface crosslinking agent encompass: polyols such as pentanediol, hexanediol, and sorbitol; polyglycidyl compounds such as (poly)ethylene glycol diglycidyl ether and glycerin polyglycidyl ether; polyamines such as a polyamide polyamine-epihalohydrin adduct (trade name: Kymene, manufactured by Hercules Incorporated) and polyethylene imine; and the like. The another surface crosslinking agent is also exemplified by, for example, a polyvalent metal salt that is classified as an additive (described later). In particular, use of the organic surface crosslinking agent in combination with a polyol or a polyglycidyl compound is preferable, and use of the organic surface crosslinking agent in combination with a polyglycidyl compound is more preferable.

The organic surface crosslinking agent and the another surface crosslinking agent are used, in an amount (total weight in all steps of adding the organic surface crosslinking agent) preferably of 0.001 parts by weight to 15 parts by weight, more preferably of 0.001 parts by weight to 10 parts by weight, and even more preferably of 0.01 parts by weight to 5 parts by weight, based on 100 parts by weight of the water-absorbing resin powder.

In a case where two types of compounds, i.e., a polyhydric alcohol compound and a compound selected from compounds different from the polyhydric alcohol compound are used as the organic surface crosslinking agent, the polyhydric alcohol compound is used in an amount (total weight in all steps of adding the organic surface crosslinking agent) preferably of 0.001 parts by weight to 10 parts by weight and more preferably of 0.01 parts by weight to 5 parts by weight, based on 100 parts by weight of the water-absorbing resin powder. Further, a compound different from the polyhydric alcohol compound is used in an amount (total weight in all steps of adding the organic surface crosslinking agent) preferably of 0.001 parts by weight to 10 parts by weight and more preferably of 0.01 parts by weight to 5 parts by weight, based on 100 parts by weight of the water-absorbing resin powder.

(Preparation of Organic Surface Crosslinking Agent Solution)

The organic surface crosslinking agent can be used as it is. Note, however, that the organic surface crosslinking agent is preferably used in a form of an organic surface crosslinking agent solution so that the organic surface crosslinking agent is more uniformly added. A temperature of a solvent for use in preparation of the organic surface crosslinking agent is appropriately determined. Note, however, that a too low temperature may make solubility and viscosity too low. For example, in a case where a solid non-macromolecular organic compound, particularly ethylene carbonate is used as the organic surface crosslinking agent, a solvent therefor is warmed to have a temperature preferably of not lower than 10° C., more preferably of 30 to 100° C., even more preferably of 35 to 70° C., and most preferably of 40 to 65° C.

(Solvent and Concentration)

The solvent preferably contains water. That is, the organic surface crosslinking agent solution is preferably an aqueous organic surface crosslinking agent solution. The water is used in an amount (total weight in all steps of adding the organic surface crosslinking agent) preferably of 0.5 parts by weight to 20 parts by weight and more preferably of 0.5 parts by weight to 10 parts by weight, based on 100 parts by weight of the water-absorbing resin powder. Note that the water also includes crystalline water, hydrated water, and the like of the organic surface crosslinking agent.

Further, the organic surface crosslinking agent solution can contain a hydrophilic organic solvent. The hydrophilic organic solvent is used in an amount preferably of more than 0 part by weight and not more than 10 parts by weight and more preferably of more than 0 part by weight and not more than 5 parts by weight, based on 100 parts by weight of the water-absorbing resin powder. Examples of the hydrophilic organic solvent encompass preferably a $C_1$-$C_4$ primary alcohol, more preferably a $C_2$-$C_3$ primary alcohol, other lower ketones whose carbon number is 4 or lower, such as acetone, and the like. As the hydrophilic organic solvent, a volatile alcohol having a boiling point preferably of lower than 150° C. and more preferably of lower than 100° C. is more preferable. This is because such a volatile alcohol evaporates during the surface crosslinking treatment and thus no residue lingers.

Specific examples of the hydrophilic organic solvent encompass: monohydric alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as epsilon-caprolactam and N,N-dimethylformamide; sulfoxides such as dimethyl sulfoxide; and the like.

Note that the surface crosslinking agent C2 compound and the surface crosslinking agent C3 compound each also include a compound that is used as the hydrophilic organic solvent. For example, the specification of U.S. Pat. No. 5,597,873 and Japanese Patent Application Publication, Tokukaihei, No. 9-67522 each disclose a technique for in using a glycidyl compound such as ethylene glycol diglycidyl ether as a surface crosslinking agent, using ethylene glycol, propylene glycol, or 1,3-propanediol as a solvent therefor. Note, however, that such a compound is treated as a surface crosslinking agent in the present invention provided that the compound is used in the surface crosslinking step, particularly provided that the compound has a gas density falls within a range of the gas density of the present invention.

It can be appropriately confirmed by, for example, a reduction in fluid retention capacity, IR, and/or hydrolysis that the hydrophilic organic solvent reacts, as a surface crosslinking agent, with a functional group of a water-absorbing resin.

Further, the organic surface crosslinking agent solution can contain a water-insoluble microparticle and a surfactant. Specifically, the water-insoluble microparticle and the surfactant can coexist in an amount of more than 0 part by weight and not more than 10 parts by weight, preferably of more than 0 part by weight and not more than 5 parts by weight, and more preferably of more than 0 part by weight and not more than 1 part by weight, based on 100 parts by weight of a water-absorbing resin powder. In this case, a surfactant or the like disclosed in the specification of, for example, U.S. Pat. No. 7,473,739 can be used as the surfactant or the like of the present invention.

A concentration of an organic surface crosslinking agent contained in the organic surface crosslinking agent solution is appropriately determined. In terms of a total amount of all organic surface crosslinking agents contained in respective organic surface crosslinking agent solutions used in all addition processes, the organic surface crosslinking agent contained in the organic surface crosslinking agent solution of the present invention in a form of an aqueous solution has a concentration preferably of 1 weight % to 80 weight %, more preferably of 5 weight % to 60 weight %, even more preferably of 10 weight % to 40 weight %, and especially even more preferably of 15 weight % to 30 weight %. Note that the hydrophilic organic solvent and/or other component(s) can be contained as a residue.

A temperature of the organic surface crosslinking agent solution is appropriately determined based on, for example, solubility of an organic surface crosslinking agent to be used, or viscosity of the organic surface crosslinking agent solution. The temperature of the organic surface crosslinking agent solution ranges preferably from −10 to 100° C., more preferably from 5 to 70° C., even more preferably from 10 to 65° C., and especially even more preferably from 25 to 50° C. The organic surface crosslinking agent solution which has a high temperature is not preferable. This is because such an organic surface crosslinking agent solution that has not been mixed or reacted with a water-absorbing resin powder may cause (1) in a case where the organic surface crosslinking agent is a cyclic organic surface crosslinking agent, hydrolysis of the cyclic surface crosslinking agent (e.g., degradation from ethylene carbonate into ethylene glycol, degradation from oxazolidinone into ethanolamine) and (2) a deterioration in mixability by, for example, volatilization of water and a hydrophilic organic solvent that are contained in the organic surface crosslinking agent solution. Meanwhile, the organic surface crosslinking agent solution which has a too low temperature may cause (3) solidification of the organic surface crosslinking agent solution and (4) precipitation of the organic surface crosslinking agent.

(Addition of Acid or Base)

The organic surface crosslinking agent solution can contain an acid or a base as well as the organic surface crosslinking agent, the hydrophilic organic solvent, the surfactant, and the water-insoluble microparticle so as to promote reaction and uniform mixing of the organic surface crosslinking agent.

As the acid or the base, an organic acid or a salt thereof, an inorganic acid or a salt thereof, or an inorganic base can be used. The acid or the base is appropriately used in an amount falling within a range preferably of 0 part by weight to 10 parts by weight, more preferably of 0.001 parts by weight to 5 parts by weight, and even more preferably of 0.01 parts by weight to 3 parts by weight, based on 100 parts by weight of the water-absorbing resin powder. The organic acid is preferably a $C_1$-$C_6$ water-soluble organic acid, more preferably a $C_2$-$C_4$ water-soluble organic acid, a water-soluble saturated organic acid, a saturated organic acid containing a hydroxyl group, and especially even more preferably a saturated organic acid containing a hydroxyl group.

Other examples of the acid or the base encompass: non-crosslinkable water-soluble inorganic bases (preferably, an alkali metal salt, an ammonium salt, a hydroxide of an alkali metal, and an ammonia or a hydroxide thereof); non-reducible alkali metal salt pH buffers (preferably bicarbonate, dihydrogen phosphate, hydrogen phosphate, and the like); and the like.

(Method for Adding Organic Surface Crosslinking Agent Solution)

The organic surface crosslinking agent is added to a water-absorbing resin powder by an addition process. A method for carrying out the addition process is exemplified by but not particularly limited to, for example, (1) a method of immersing a water-absorbing resin powder in a hydrophilic organic solvent so as to cause an organic surface crosslinking agent to adsorb to the water-absorbing resin powder, and (2) a method of spraying or dropping an organic surface crosslinking agent solution directly to a water-absorbing resin powder so as to mix the water-absorbing resin powder with the organic surface crosslinking agent solution. From the viewpoint of uniform addition of a predetermined amount of an organic surface crosslinking agent to a water-absorbing resin powder, the method (2) is more preferable. Further, in order that the organic surface crosslinking agent is uniformly added to the water-absorbing resin powder, the addition process is preferably carried out while the water-absorbing resin powder is being stirred, and the addition process is more preferably carried out by spraying the organic surface crosslinking agent.

In a case where two or more types of organic surface crosslinking agents having respective different compositions are used in the addition process, different spray nozzles, for example can be used to simultaneously add the organic surface crosslinking agents. Note, however, that from the viewpoint of uniform addition of the organic surface crosslinking agents, it is preferable that the organic surface crosslinking agents be added after being adjusted to have a single composition. Further, in a case where the organic surface crosslinking agents have a single composition, a plurality of spray nozzles can be used in consideration of, for example, a size and throughput of an apparatus for use in the addition process, and a spray angle of a spray nozzle.

Preferable examples of the apparatus for use in the addition process (hereinafter also referred to as a "mixing apparatus) encompass a cylindrical mixing apparatus, a double-wall conical mixing apparatus, a V-shaped mixing apparatus, a ribbon mixing apparatus, a screw mixing apparatus, a flow furnace, a rotary disc mixing apparatus, an airflow mixing apparatus, a double-arm kneader, an internal mixing apparatus, a pulverizing kneader, a rotary mixing apparatus, a screw extruder, a turbulizer, a ploughshare mixing apparatus, and the like. Further, in large-scale production such as commercial production, the mixing apparatus is preferably an apparatus capable of carrying out continuous mixing. Still further, the addition processes can be carried out by use of either an identical apparatus or respective different apparatuses.

A water-absorbing resin powder to be subjected to the present step is preferably heated or kept warm. The water-absorbing resin powder has a temperature falling within a range preferably of 30 to 100° C., more preferably of 35 to 90° C., and even more preferably of 50 to 80° C. The water-absorbing resin powder which has a low temperature may cause, for example, an insufficient or non-uniform surface treatment with respect to the water-absorbing resin powder due to, for example, precipitation of a surface crosslinking agent and/or moisture absorption of the water-absorbing resin powder. The water-absorbing resin powder which has an extremely high temperature, particularly a temperature higher than a boiling point of water in a case where the organic surface crosslinking agent solution is an aqueous organic surface crosslinking agent solution may cause, for example, precipitation of the organic surface crosslinking agent due to, for example, evaporation of water contained in the aqueous organic surface crosslinking agent solution. Further, a mixture, obtained through the present step, of the organic surface crosslinking agent solution and the water-absorbing resin powder has a temperature falling within a range preferably of 30 to 100° C., more preferably of 35 to 90° C., and even more preferably of 40 to 80° C. The mixture which has a temperature falling within the above range yields an effect of (i) allowing an added organic surface crosslinking agent to be effectively reacted in the subsequent surface crosslinking step and (ii) allowing moderate fluidity of the mixture to be maintained.

(2-8) Surface Crosslinking Step

The present step is a step of in order to achieve a water absorbing speed, a fluid retention capacity under load, liquid permeability, and salt tolerance of a water-absorbing agent, carrying out a heat treatment for uniformly providing a water-absorbing resin powder with a thick and high-density crosslinked layer having a strong uppermost surface. The present step can be carried out simultaneously with the surface crosslinking agent addition step or after the surface crosslinking agent addition step. It is more preferable from the viewpoint of quality stabilization that the present step be carried out after the surface crosslinking agent addition step. From the viewpoint of stable production, the present step is carried out preferably within 10 seconds, more preferably within 5 seconds, and even more preferably within 3 seconds of an end of the surface crosslinking agent addition step.

In the production method in accordance with the present invention, the present step can be carried out once or can be carried out a plurality of times under an identical condition or under different conditions. Note, however, that a water-absorbing agent in accordance with the present invention can be obtained by carrying out the present step at least one time in an atmosphere that is controlled so that the atmosphere has a specific organic surface crosslinking agent concentration.

(Heating Apparatus)

A heating apparatus used in the present invention is exemplified by a continuous type heating apparatus and a batch type heating apparatus each including a publicly known dryer or a publicly known heating furnace that is provided with a gas discharge mechanism and/or a gas supply mechanism for causing the dryer or the heating furnace to have a predetermined atmosphere, and the continuous type heating apparatus is more preferable.

A heating method by which the heating apparatus carries out heating is suitably exemplified by conductive heat transfer, radiative heat transfer, hot-air heat transfer, and dielectric heating. The heating method is preferably conductive heat transfer and/or hot-air heat transfer, and more preferably conductive heat transfer.

Further, in order to enhance heating efficiency and carry out a uniform heat treatment, it is preferable to use an apparatus including a mechanism for continuously stirring and/or fluidizing an object to be heated. A stirring and/or fluidizing method is preferably a groove stirring method, a method of a screw type, a method of a rotary type, a method of a disc type, a method of a kneading type, a method of a fluidized-bed type, or the like. The stirring and/or fluidizing method is more preferably (i) a stirring method carried out by use of a stirring blade (paddle) or (ii) a stirring method (such as a rotary retort furnace) carried out by movement of a heat transfer surface itself. Note that the mechanism for continuously stirring and/or fluidizing an object to be heated, which mechanism is intended to carry out a uniform heat treatment, does not need to be used in a case where an amount of an object to be heat-treated is small, e.g., in a case where an object to be dried has a thickness of less than 1 cm.

The heating apparatus includes the gas discharge mechanism for discharging vapor generated from an object to be heated and is also capable of controlling a gas density, a water vapor density, and a temperature of a heating section (an inside of the heating apparatus) by adjusting the gas discharge mechanism, e.g., by adjusting an amount of discharge of vapor to be discharged from the object to be heated. Note that the heating section is not a so-called heat source such as a heater or a dielectric coil but a place in which to increase a temperature of the object to be heated.

Not only merely an air outlet but also an outlet for a heat-treated object through which outlet gas is to be discharged corresponds to the gas discharge mechanism. Further, the gas discharge mechanism preferably uses a blower or the like to adjust an amount of and a pressure of gas to be discharged. Still further, the heating apparatus does not need to be provided with only one air outlet and can be provided with a plurality of air outlets in consideration of a size of the heating apparatus and how a temperature of the heating apparatus is adjusted.

The adjustment in atmospheric temperature (described earlier) can also be carried out by use of a part of a heating portion of the heating apparatus, in which part a water-absorbing resin powder serving as an object to be heated is absent. In this case, it is possible to increase efficiency with which to heat gas (gas to be supplied) by use of filler such as a metallic ring-shaped object, a metallic mesh-shaped object, a ceramic ring-shaped object, or a ceramic mesh-shaped object.

In carrying out industrial continuous production, it is possible to use a batch processing type (batch type) or continuous processing type heating apparatus including the mechanism (described earlier).

Examples of a method used in the batch processing type heating apparatus encompass: a method of leaving an object to be heated at rest on, for example, one or more trays so that the object to be heated is substantially equally distributed over, for example, the one or more trays; a method of filling a single bath or a plurality of baths with an object to be heated and then heating the object to be heated while stirring the object to be heated with a stirring blade or the like; (iii) a method of filling a fluidized bed with an object to be heated and then heating the object to be heated while stirring the object to be heated with a stirring blade or the like; and the like. Meanwhile, examples of a method used in the continuous processing type heating apparatus encompass: a method of conveying an object to be heated which is substantially equally distributed over a belt or a plurality of trays: a method of conveying an object to be heated while stirring the object to be heated with a stirring blade, a screw, or the like; a method of conveying an object to be heated by use of an inclined heating surface; and the like.

Specifically, a heating apparatus of the present invention is preferably a conductive heat transfer type heating apparatus in which steam under pressure (high pressure steam) is used as a heat source and which includes a continuous stirring mechanism. Further, in order that continuous production is efficiently carried out, the heating apparatus of the present invention preferably has a downward inclination (of more than 0 degree relative to a horizontal plane) which allows an object to be heated to be subjected to a gravity flow toward an outlet of the object to be heated. The heating apparatus which has a downward inclination of a too great angle may cause a variation in heating time. Thus, the heating apparatus has an inclination preferably of more than 0 degree and not more than 20 degrees and more preferably of more than 0 degree and not more than 10 degrees, relative to the horizontal plane.

In a case where the addition processes are carried out before the heat treatment and after the heat treatment, respectively, the addition process after the heat treatment can be carried out by an apparatus identical to or different from an apparatus used to carry out the addition process before the heat treatment. Particularly in a case where a continuous type production apparatus is used, it is preferable in terms of production efficiency that the addition process before the heat treatment and the heat treatment be carried out by use of a single apparatus and the addition process after the heat treatment be carried out by use of an apparatus different from an apparatus used to carry out the heat treatment.

Further, it is also possible to use a plurality of heating apparatuses in which identical or different heating methods (described earlier), identical or different stirring methods (described earlier), identical or different gas discharge methods (described earlier), and identical or different gas supply methods (described earlier) are combined.

Regarding control of an atmospheric temperature (described later), a concentration of an organic surface crosslinking agent, and a water vapor density, it is only necessary to appropriately control the amount of gas to be discharged (described earlier), a temperature of gas to be supplied, and a flow rate in consideration of (i) heat transfer from a wall surface of a heating apparatus or from a water-absorbing resin powder, (ii) a change in concentration of the organic surface crosslinking agent due to the vaporized organic surface crosslinking agent and water vapor each generated from the water-absorbing resin powder in the heating apparatus, and (iii) a rise in dew point.

(Controlled Temperature of Heating Apparatus)

A controlled temperature of the heating apparatus only needs to allow a water-absorbing resin powder to be heated to a temperature (described later), and does not need to be constant throughout the surface crosslinking step. Note, however, that in order to prevent, for example, partial overheating, the heating apparatus has a temperature preferably of 100 to 300° C., more preferably of 120 to 280° C., even more preferably of 150 to 250° C., and especially even more preferably of 170 to 230° C. for not less than 70% of, particularly not less than 90% of, substantially throughout a time period from a start to an end of the present step.

(Gas Density and Water Vapor Density of Organic Surface Crosslinking Agent)

A gas density as used in the present invention refers to a value obtained by dividing, by an amount of noncondensable gas, a weight of a condensable compound contained in gas, and has a dimension of "weight/volume". Specifically, a weight of a condensable compound that is collected from sampled gas by cooling or solvent absorption is measured, and an amount of the remaining noncondensable gas is measured by use of a gas meter or the like. A gas density is calculated by dividing the weight of the collected condensable compound by a volume of the noncondensable gas whose amount has been converted to a normal state of 0° C. and 1 atmosphere. Further, a water vapor density refers to a gas density on the condition that a condensable compound is water.

The gas density (water vapor density) can be adjusted by adjusting an amount of and a kind of the gas to be supplied, and further an amount of a component contained in the gas to be supplied. Specifically, the gas density can be appropriately adjusted by, for example, (i) a method of adjusting an amount of supply of noncondensable gas such as air or nitrogen by supplying only that noncondensable gas, (ii) a method of adjusting an amount of supply of gas of (a) an organic surface crosslinking agent, which is a condensable compound, and/or (b) water by supplying only that gas, or (iii) a method of adjusting an amount of a gas mixture of a condensable compound and noncondensable gas by supplying that gas mixture, and further adjusting a mixing ratio of the gas mixture.

On an industrial scale, a method of adjusting an amount of supply of noncondensable gas or a method of adjusting an amount of a gas mixture is easily carried out. As noncondensable gas that is preferably used, air or nitrogen, or a gas mixture of air and nitrogen is suitable.

Note that "noncondensable gas" as used in the present invention refers to gas in a normal state of 0° C. and 1 atmosphere.

The present invention is arranged such that for at least five minutes of a start of raising a temperature of the water-absorbing resin powder, the surface crosslinking agent C2 compound and/or the surface crosslinking agent C3 compound have/has a gas density of at least 0.01 g/L, more preferably of at least 0.015 g/L, and even more preferably of at least 0.02 g/L. In a case where the surface crosslinking agent C4 compound is used, it is preferable that the surface crosslinking agent C4 compound also have a gas density falling within a range similar to the above range. Further, in a case where two or more kinds of the surface crosslinking agent C2 compound, the surface crosslinking agent C3 compound, and the surface crosslinking agent C4 compound are used in combination, the surface crosslinking agent C2 compound, the surface crosslinking agent C3 compound, and/or the surface crosslinking agent C4 compound each have a gas density of at least 0.01 g/L, more preferably of at least 0.015 g/L, and even more preferably of at least 0.02 g/L. The gas density of less than 0.01 g/L makes it impossible to obtain an intended effect of the present invention.

In addition, the surface crosslinking agent C2 compound and/or the surface crosslinking agent C3 compound have/has a gas density preferably of 0.1 g/L or less, more preferably of 0.075 g/L or less, and even more preferably of 0.05 g/L or less. In a case where the surface crosslinking agent C4 compound is used, it is preferable that the surface crosslinking agent C4 compound also have a gas density falling within a range similar to the above range. Further, in a case where two or more kinds of the surface crosslinking agent C2 compound, the surface crosslinking agent C3 compound, and the surface crosslinking agent C4 compound are used in combination, the surface crosslinking agent C2 compound, the surface crosslinking agent C3 compound, and/or the surface crosslinking agent C4 compound each have a gas density preferably of 0.1 g/L or less, more preferably of 0.075 g/L or less, and even more preferably of 0.05 g/L or less.

A typical range of each of the above gas densities, which typical range is appropriately selectable within a range of the above upper limit to the above lower limit, is preferably from 0.01 g/L to 0.1 g/L, more preferably from 0.01 g/L to 0.075 g/L, even more preferably from 0.015 g/L to 0.075 g/L, and especially even more preferably from 0.02 g/L to 0.05 g/L.

Further, in a case where the another organic surface crosslinking agent is used, all the organic surface crosslinking agents have a gas density preferably of 0.1 g/L or less, more preferably of 0.075 g/L or less, and even more preferably of 0.05 g/L or less. In a case where the gas density is more than 0.1 g/L, it may be impossible to obtain an effect that is in line with the total amount of all organic surface crosslinking agents, a deterioration in effect may occur, and further there may also be a risk of, for example, ignition.

In addition, in a case where the another organic surface crosslinking agent is used, all the organic surface crosslinking agents have a gas density preferably of at least 0.01 g/L, more preferably of at least 0.015 g/L, and even more preferably of at least 0.02 g/L. Thus, a typical range of the gas density of all the organic surface crosslinking agents, which typical range is appropriately selectable within a range of the above upper limit to the above lower limit, is preferably from 0.01 g/L to 0.1 g/L, more preferably from 0.015 g/L to 0.1 g/L, and even more preferably from 0.02 g/L to 0.1 g/L.

In a case where the another organic surface crosslinking agent is degraded to fall under any of the surface crosslinking agent C2 compound, the surface crosslinking agent C3 compound, and the surface crosslinking agent C4 compound, which are described earlier, compounds obtained after the degradation each have a gas density falling within such a typical range as mentioned above.

The water vapor density falls within a range preferably of 0.3 g/L to 1.5 g/L, more preferably of 0.4 g/L to 1.3 g/L, and even more preferably of 0.5 g/L to 1.1 g/L. The water vapor density which falls outside the above range may make it impossible to obtain a desired effect and thus is not preferable.

A gas density of the organic surface crosslinking agent and a water vapor density each vary in accordance with a position in the heating section and passage of a heating time and each preferably fall within a predetermined range in the heating apparatus. A variation of the gas density of the organic surface crosslinking agent is preferably not more than 0.005 g/L, and a variation of the water vapor density of the organic surface crosslinking agent is preferably not more than 0.05 g/L.

The amount of noncondensable gas is preferably 1000 $Nm^3$/ton or less and more preferably 200 $Nm^3$/ton as a rate based on a weight of a mixture to be subjected to a heat treatment. Note that the amount of noncondensable gas may fall outside the above ratio in a case where the heating apparatus is not in a steady state in continuous production, i.e., at a start and an end of operation of the heating apparatus.

It is preferable to control an airflow in the heating section so that air flows in a constant direction. In particular, in a case where an apparatus capable of continuous processing is used, a direction of an airflow is preferably a vertical direction or a horizontal direction, more preferably the horizontal direction even more preferably a countercurrent flow and/or a concurrent flow, and especially even more preferably the concurrent flow, with respect to a flow from an inlet toward an output for an object to be heated. Note that the term "constant direction" does not refer to an identical direction in every respect but means that a direction of a flow of a substance does not change macroscopically. For example, a partial and/or temporary turbulent or vortex state of an airflow due to, for example, stirring is not subjected to the control of an airflow in the present invention. Meanwhile, in the present invention, air does not flow in the constant direction in a case where an airflow caused by an air intake at an air inlet and an air discharge at an air outlet has been changed during a heat treatment to an airflow caused by an air intake at the air outlet and an air discharge at the air inlet.

In a case where a large-sized heating apparatus includes a plurality of gas discharge ports and a plurality of gas supply ports, particularly in a case where a continuous processing type heating apparatus is used, for example, coexistence of a point of a countercurrent flow and a point of a concurrent flow in the heating section does not matter provided that an airflow does not change in direction over time at each point.

The heating section preferably has a pressure that is slightly reduced from a normal atmospheric pressure (101.3 kPa (1 atmosphere)). The pressure differs from atmospheric pressure around the heating apparatus preferably by −10 kPa to 0 kPa, more preferably by −5 kPa to 0 kPa, and even more preferably by −2 kPa to 0 kPa.

(Heating Condition)

In order to sufficiently obtain the effect of the present invention, until a temperature of a water-absorbing resin powder is increased to a temperature not lower than 170° C., more preferably to 160° C., even more preferably to 150° C., and especially even more preferably to 140° C., heating apparatus has (i) the gas density of the organic surface crosslinking agent which gas density falls within the above range and (ii) the water vapor density which falls within the above range. Further, in order to enhance the effect of the present invention, the temperature of the water-absorbing resin powder reaches the above increased temperature, i.e., the temperature of the water-absorbing resin powder starts to be increased and then reaches the above increased temperature preferably in a time not shorter than five minutes.

A gas phase part of the heating section has a temperature preferably of 100 to 300° C., more preferably of 100 to 200° C., and even more preferably of 100 to 150° C.

The water-absorbing resin powder, which is an object to be heated, only needs to have a maximum temperature at which the organic surface crosslinking agent and a functional group of the water-absorbing resin powder can react with each other. The maximum temperature is preferably 175 to 300° C., more preferably 175 to 250° C., and especially even more preferably 180 to 230° C. The maximum temperature which is lower than 175° C. may cause a covalent bond for surface crosslinking to be insufficiently formed. The maximum temperature which is higher than 300° C. may cause a deterioration in water-absorbing resin to be obtained.

A solid content (%) of a water-absorbing resin before and after surface crosslinking can be changed. That is, the solid content of the water-absorbing resin before the surface crosslinking agent addition step (i.e., the solid content after the drying step) can be equal to, higher than, or lower than the solid content of the water-absorbing resin after surface crosslinking. In order to maximize the effect of the present invention, it is preferable to use the dehydration reactive surface crosslinking agent to (i) make the solid content after surface crosslinking lower than the solid content before surface crosslinking by not less than 2 weight % or (ii) make the solid content after the present step (surface crosslinking step) lower than the solid content before the present step (surface crosslinking step) by not less than 2 weight %.

Note that a time of the heat treatment is not particularly limited provided that the temperature condition (described earlier) is satisfied. Note, however, that the time is normally 1 minute to 120 minutes and preferably 5 minutes to 60 minutes.

Further, for the purpose of prevention of an excessive crosslinking reaction and an improvement in handleability in a subsequent step, the water-absorbing resin taken out of the heating apparatus can be appropriately cooled to a temperature preferably of lower than 100° C., more preferably of 0 to 95° C., and even more preferably of 40 to 90° C.

(Amount of Residual Surface Crosslinking Agent after End of Heat Treatment)

In a case where the effect of the present invention is exhibited, the surface crosslinking agent is prevented from evaporating during the heat treatment. This causes an increase in amount of a residual surface crosslinking agent contained in water-absorbing resin particles which have been subjected to the heat treatment. In this regard, the surface crosslinking step of the present invention is carried out so that a "residual ratio of the surface crosslinking agent" (amount of organic surface crosslinking agent remaining after surface crosslinking/amount of organic surface crosslinking agent added) is preferably not less than 0.5, more preferably not less than 0.6, and even more preferably not less than 0.7. The surface crosslinking step of the present invention is also carried out so that the residual ratio of the surface crosslinking agent has an upper limit preferably of less than 1.0, more preferably of less than 0.9, and even more preferably of less than 0.8. Thus, the surface crosslinking step of the present invention is carried out so that a typical range of the residual ratio of the surface crosslinking agent, which typical range is appropriately selectable within a range of the above upper limit to the above lower limit, is preferably not less than 0.5 and less than 1.0, more preferably not less than 0.5 and less than 0.9, even more preferably not less than 0.6 and less than 0.9, and especially even more preferably not less than 0.7 and less than 0.8.

It is considered that during the heat treatment, the surface crosslinking agent significantly evaporates immediately after the water-absorbing resin powder is introduced into the heating apparatus, the water-absorbing resin powder containing the organic surface crosslinking agent a large amount of which is unreacted and is present in a surface and its vicinity of the water-absorbing resin powder. Thus, since the water-absorbing agent of the present invention is arranged such that (i) evaporation of the organic surface crosslinking agent is prevented particularly at an early stage and (ii) a strong crosslinked layer is formed, surface crosslinking further progresses in the water-absorbing agent of the present invention than in a conventional water-absorbing agent even in a case where the water-absorbing agent of the present invention is identical in residual amount of the organic surface crosslinking agent to the conventional water absorbent. Specifically, the water-absorbing agent of the present invention and the conventional water-absorbing agent have a relationship as shown in the graph of FIG. 1, which graph shows results of Example 2 and Comparative Example 2 that are described later.

The residual surface crosslinking agent and a residual by-product were measured as below. That is, 1 g of a water-absorbing resin was allowed to swell in a 0.9 weight % aqueous sodium chloride solution (saline), and a resultant solution was stirred for one hour. Then, the resultant solution was filtrated by use of a 0.45-μm disc filter. A filtrate thus obtained was measured by using high performance liquid chromatography (HPLC) to calculate a residual amount based on a weight of a water-absorbing resin. Note that a detection limit (N.D. level) was not more than 100 ppm. Note also that a sample amount of the water-absorbing resin refers to a solid content of 1 g in view of a moisture content. That is, for example, a water-absorbing resin having a moisture content of 10 weight % is used in an amount of 1.1 g.

In the present invention, assuming that (i) an "amount (g/g) of decrease in fluid retention capacity (CRC) caused by surface crosslinking" and (ii) a "residual ratio (g/g) of surface crosslinking agent" (i.e., amount of organic surface crosslinking agent remaining after surface crosslinking/amount of organic surface crosslinking agent added) of the water-absorbing agent which are obtainable by changing a heat treatment time, are an objective variable X and an explanatory variable Y, respectively, it is revealed that an intercept b (b in Y=aX+b), which is obtainable by regression analysis by a least squares method, is as high as not less than 0.8. That is, it is revealed that the organic surface crosslinking agent remains in a large amount by carrying out the heat treatment under a condition that the surface crosslinking agent C2 compound or the surface crosslinking agent C3 compound has a gas density of at least 0.01 g/L in the gas phase part of the heating apparatus, so that the effect of the present invention is obtained.

In order that the effect of the present invention is further exhibited, the heat treatment is preferably carried out under a selected condition that the intercept b has a value of not less than 0.85, and is more preferably carried out under a selected condition that the intercept b has a value of not less than 0.9.

Note that the regression analysis is carried out by use of data obtained at four points that correspond to respective intervals between 1.9 g/g and 2.1 g/g, between 2.9 g/g and 3.1 g/g, between 3.9 g/g and 4.1 g/g, and between 4.9 g/g and 5.1 g/g, in each of which intervals the amount (X) of decrease in fluid retention capacity is obtained.

(Method for Measuring Gas Density)

The temperature of the gas phase part of the heating section, and the gas density of the organic surface crosslinking agent and the water vapor density have values measured in the atmosphere (described earlier) vertically above the water-absorbing resin powder which is being heated in the heating section. These values are measured by collecting gas located within 5 cm, preferably 3 cm, and more preferably 1 cm from a powder surface of the water-absorbing resin powder.

Examples of a method for collecting the gas encompass (i) a method in which the gas is collected in a cylindrical container having a moderate capacity and (ii) a method in which the gas is sucked by use of a pump and the organic surface crosslinking agent or water vapor is condensed or absorbed during the sucking. The method (ii) is preferable for accurate measurement. Preferable examples of a specific apparatus for collecting the gas encompass an apparatus arranged as below.

Specifically, the apparatus is arranged to include (i) a hard sampling line which has an inner diameter of approximately 1 mm to 10 mm, which has thermal resistance and chemical resistance, and which is preferably a tube made of stainless steel, (ii) a gas switching section which is preferably a hexagonal valve having thermal resistance, (iii) a trap section for condensing or absorbing a condensable component, (iv) a flow rate measurement section for measuring a flow rate of noncondensable gas which has passed through the trap section, and (v) a suction pump connected to a downstream of the flow rate measurement section. Further, the apparatus has a part which is upstream from the trap section and whose temperature can be maintained preferably at a temperature of not lower than a temperature of gas collected at an entrance of the sampling line, more preferably at a temperature of not lower than 100° C., and even more preferably at a temperature of 100 to 150° C. In a case where powder dust causes, for example, clogging, it is preferable to provide the sampling line with, for example, a filter or a cyclone dust collector.

The collected gas only needs to have a flow rate preferably of not longer than 10 seconds, more preferably of not longer than 5 seconds, and even more preferably of not longer than 3 seconds, the flow rate being obtained by dividing, by a flow rate of noncondensable gas, a capacity of a space between the entrance of the sampling line and an entrance of the flow rate measurement section.

A weight of a collected condensable compound only needs to be quantitatively determined by, for example, gas chromatography or liquid chromatography. A weight of water can be calculated by, for example, Kerl Fischer titration method.

(Conventional Technique)

Patent Literatures 1 through 71 fail to disclose the gas density of the gas phase part during surface crosslinking carried out in the present invention. Meanwhile, Patent Literatures 72 through 74 each propose a technique for directly carrying out surface crosslinking with respect to a water-absorbing resin by use of a gaseous surface crosslinking agent.

Note, however, that the technique disclosed in each of Patent Literatures 72 through 74 is merely a technique for directly carrying out surface crosslinking with respect to a water-absorbing resin by use of a gaseous surface crosslinking agent. Unlike the present invention, none of Patent Literatures 72 through 74 focus on a gas density during a heat treatment, i.e., after addition of a surface crosslinking agent and water to a water-absorbing resin powder. Thus, as shown in Comparative Example 5 of the present invention, the object of the present invention is not attained by such conventional techniques.

(2-9) Additive Addition Step

In the production method of the present invention, it is preferable to add an additive selected from additives (liquid permeability improving agents), particularly from water-insoluble fine particulate compounds and polyvalent cationic compounds. The step of adding the additive selected from the water-insoluble fine particulate compounds and the polyvalent cationic compounds can be carried out simultaneously with the surface crosslinking agent addition step or can be carried out after the surface crosslinking step.

"Carrying out the step of adding the additive simultaneously with the surface crosslinking agent addition step" is any of the following (a) through (c): (a) adding the additive which has been mixed with the organic surface crosslinking agent or the organic surface crosslinking agent solution; (b) adding, simultaneously with addition of the organic surface crosslinking agent or the organic surface crosslinking agent solution, the additive which is not mixed with the organic surface crosslinking agent or the organic surface crosslinking agent solution; and (c) adding the additive at a stage before the surface crosslinking agent addition step, and is also a combination of two or more of the above (a) through (c).

In a case where the surface crosslinking agent addition step and the additive addition step are each carried out two or more times, it is more preferable that the last surface crosslinking agent addition step be carried out before the last additive addition step, and it is even more preferable that the first additive addition step be carried out after the first surface crosslinking agent addition step. Note that in a case where the additive is added only one time, such an additive addition step is the first addition step and is also the last addition step.

This is exemplified by, for example, the following modes: a mode in which the additive addition step is carried out after the surface crosslinking agent addition step; a mode in which the surface crosslinking agent addition step and the additive addition step are simultaneously carried out; a mode in which the surface crosslinking agent addition step and the additive addition step are simultaneously carried out and then the additive addition step is further carried out; and the like.

The surface crosslinking step only needs to be carried out after the first surface crosslinking agent addition step. It is preferable that the surface crosslinking step be carried out at least one time after the surface crosslinking agent addition step is carried out at least one time, and it is more preferable that the surface crosslinking step be carried out one time after the surface crosslinking agent addition step is all carried out.

In the present invention, in which an additive selected from water-insoluble fine particulate compounds and polyvalent cationic compounds is used to exhibit an effect while serving preferably as a liquid permeability improving agent or an anti-caking agent, particularly as a liquid permeability improving agent, such an additive may be hereinafter collectively referred to as a "liquid permeability improving agent" in this specification in consideration of a typical function of an additive.

Further, it is also possible in the present invention to regard, as "another surface crosslinking agent", a crosslinkable additive such as a water-soluble polyvalent metal cation-containing compound (described later).

(Liquid Permeability Improving Agent)

The liquid permeability improving agent as used in the present invention refers to (i) an additive selected from water-insoluble fine particulate compounds and polyvalent cationic compounds or (ii) an additive which further increases an SFC or gel bed permeability (GBP) (preferably further increases an SFC in a range described later) as compared with a case where no liquid permeability improving agent is used. Note that the term "GBP" is defined in International Publication No. WO 2004/096304.

A water-insoluble fine particulate compound and a polyvalent cationic compound which are used in the present invention each serve as a stereoscopic spacer or an electrostatic spacer on a surface of a water-absorbing resin and a surface of water-absorbing resin particles, and allow a water-absorbing agent to be obtained to have "higher liquid permeability (e.g., an increase in SFC (described later) preferably by not less than $1\times10^{-7}\cdot cm^3\cdot s\cdot g^{-1}$ and more preferably by not less than $10\times10^{-7}\cdot cm^3\cdot s\cdot g^{-1}$ as compared with an SFC obtained in a case where no liquid permeability improving agent is used)", an "improvement in anti-caking property (e.g., an increase in blocking property during moisture absorption (described later) preferably by not less than 1% and more preferably by not less than 5%)," an "increase in gel strength", and an "increase in free swelling capacity (FSC) (e.g., an increase in FSC (defined by ERT440.2-02) preferably by not less than 0.5 g/g and more preferably by not less than 1 g/g)". Besides, an additive, depending on its kind, can carry out an action such as "deodorization and/or an antibacterial action" and/or a "reduction in residual surface crosslinking agent". Note, however, that neither an effect nor an intended use of such an action is particularly regarded as important in the present invention.

The additive (or liquid permeability improving agent) essentially added in the production method in accordance with the present invention is preferably selected from water-insoluble inorganic fine particles and polyvalent cationic compounds (cationic polymer compounds or water-soluble polyvalent metal cation-containing compounds). In this specification, a "water-soluble" compound refers to a compound that dissolves in 100 g of water at 25° C. in an amount preferably of not less than 1 g and more preferably of not less than 5 g, and a "water-insoluble" compound refers to a compound that dissolves in 100 g of water at 25° C. in an amount preferably of less than 1 g, more preferably of less than 0.5 g, and even more preferably of less than 0.1 g.

In the present invention, the organic surface crosslinking agent is crosslinked, by a covalent bond, with a functional group of a water-absorbing resin and a functional group of water-absorbing resin particles. Meanwhile, it is estimated that a polyvalent cationic compound (cationic polymer compound or water-soluble polyvalent metal cation-containing compound) of the present invention is crosslinked with a water-absorbing resin and water-absorbing resin particles by ionic crosslinking or improves liquid permeability by functioning as a stereoscopic spacer or an electrostatic spacer.

(Water-Insoluble Inorganic Fine Particles)

Examples of the water-insoluble inorganic fine particles include: water-insoluble fine particulate inorganic powders such as silicon dioxide, titanium dioxide, aluminum oxide, magnesium oxide, zinc oxide, talc, metal phosphates (e.g., calcium phosphate, barium phosphate, and aluminum phosphate), metal borates (e.g., titanium borate, aluminum borate, iron borate, magnesium borate, manganese borate, and calcium borate), silicic acid or a salt thereof, clay, diatomaceous earth, zeolite, bentonite, kaolin, hydrotalcite, and activated white clay; and organic fine powders such as calcium lactate, aluminum lactate, and metal soap (polyvalent metal salt of long chain fatty acid). The water-insoluble inorganic fine particles have a volume average particle diameter preferably of not more than 10 μm and more preferably of not more than 1 μm.

The water-insoluble inorganic fine particles can be mixed, in a form of a powder or in a form of a water dispersion (slurry (e.g., colloidal silica)), with a water-absorbing resin and water solvent resin particles. Alternatively, the water-insoluble inorganic fine particles can be dispersed in an organic surface crosslinking agent solution and then mixed with a water-absorbing resin and water-absorbing resin particles.

(Cationic Polymer Compound)

The cationic polymer compound is suitably exemplified by but not particularly limited to cationic polymer compounds disclosed in the specifications of U.S. Pat. Nos. 5,382,610, 7,098,284, International Publication No. WO 2009/110645, International Publication No. WO 2009/041731, and International Publication No. WO 2009/041727. Of the cationic polymer compounds described in the above-listed documents, polyethylene imine, polyvinyl amine, polyallylamine, or a condensate of dimethylamine, ammonia, and epichlorohydrin is preferable as the cationic polymer compound as used in the present invention.

The cationic polymer compound has a molecular weight preferably of 1,000 to 5,000,000, more preferably of 2,000 to 1,000,000, and even more preferably of 10,000 to 500,000, in terms of a weight average molecular weight.

The cationic polymer compound is preferably water-soluble from the viewpoint of facilitation of mixing. The term "water solubility" herein refers to dissolution in 100 g of water at 25° C. in an amount preferably of not less than 1 g.

The cationic polymer compound can be mixed with a water-absorbing resin and water solvent resin particles directly or in a form of a solution, particularly in a form of an aqueous solution. Alternatively, the cationic polymer compound can be mixed with a water-absorbing resin and water solvent resin particles by being dissolved in an organic surface crosslinking agent or an aqueous solution of the organic surface crosslinking agent. Further, the cationic polymer compound can be also used as the "another surface crosslinking agent" of the present invention.

(Water-Soluble Polyvalent Metal Cation-Containing Compound)

The water-soluble polyvalent metal cation-containing compound refers to a compound containing a bivalent or higher valent metal cation, preferably a trivalent or higher valent metal cation. The trivalent or higher valent metal cation is exemplified by aluminum, zirconium, and titanium. Of these trivalent or higher valent metal cations, aluminum is preferable. Examples of the water-soluble polyvalent metal cation-containing compound encompass polyvalent metal compounds such as (i) polyvalent metal inorganic salts, which are inorganic surface crosslinking agents, such as aluminum sulfate, aluminum chloride, zirconium chloride oxide, zirconium ammonium carbonate, zirconium potassium carbonate, zirconium potassium carbonate, zirconium sulfate, zirconium acetate, zirconium nitrate, and the like; (ii) polyvalent metal organic salts such as aluminum acetate, aluminum lactate, hydroxy zirconium chloride, diisopropoxybis(triethanol aminate)titanium, titanium lactate, and the like; and (iii) the like. Of these water-soluble polyvalent metal cation-containing compounds, a compound containing aluminum as the polyvalent metal cation is preferable.

The water-soluble polyvalent metal cation-containing compound can be mixed with a water-absorbing resin and water solvent resin particles directly in a form of a powder or in a form of a solution or a dispersion, particularly in a form of an aqueous solution. Alternatively, the water-soluble polyvalent metal cation-containing compound can be mixed with a water-absorbing resin and water solvent resin particles by being dissolved in an organic surface crosslinking agent or an aqueous solution of the organic surface crosslinking agent.

An additive or a liquid permeability improving agent selected from water-insoluble fine particulate compounds and polyvalent cationic compounds is used in an amount preferably of 0.001 parts by weight to 5 parts by weight, more preferably of 0.01 parts by weight to 2 parts by weight, and even more preferably of 0.01 parts by weight to 1 part by weight, based on 100 parts by weight of a water-absorbing resin to which the additive or the liquid permeability improving agent is to be added. Note that in a case where the additive or the liquid permeability improving agent is a water-soluble polyvalent metal cation-containing compound, the above values are expressed in terms of an amount of polyvalent metal cation (e.g., in a case where the additive or the liquid permeability improving agent is aluminum sulfate, the above values are defined by an amount of $Al^{3+}$).

In the production method in accordance with the present invention, a water-soluble polyvalent metal cation-containing compound can be added two or more times. For example, in a case where the water-soluble polyvalent metal cation-containing compound is added two times, a ratio between the first addition and the second addition is specified so that the ratio ranges from 1:99 to 99:1, preferably from 10:90 to 90:10. The ratio which falls outside the above range is not preferable. This is because such a ratio brings about a situation that is extremely close to a situation of one-time addition, and consequently lessens an effect of addition that is made two or more times.

Note that a non-metallic ion crosslinking agent such as a cationic polymer compound may be made tacky during the mixing (described earlier). In view of this, the non-metallic ion crosslinking agent is preferably added after the last heat treatment.

It is preferable to use water or an aqueous crosslinking agent solution as a solvent to mix the water-soluble polyvalent metal cation-containing compound. Further, it is possible to improve dispersity, solubility, and mixability by appropriately using water and a hydrophilic organic solvent (alcohol or polyglycol) and/or a surfactant in combination. An amount of water to be used is appropriately determined according to a kind of additive and an addition method. For example, the water is used in an amount preferably of 0 part by weight (dry blending) to 50 parts by weight, more preferably of 0.1 parts by weight to 10 parts by weight, and even more preferably of 0.5 parts by weight to 5 parts by weight, based on 100 parts by weight of a water-absorbing resin.

Further, examples of a suitably usable liquid permeability improving agent that is different from the liquid permeability improving agents mentioned above encompass water-soluble polysiloxane disclosed in the pamphlet of International Publication No. WO 2009/093708, primary to tertiary amine compounds disclosed in the pamphlet of International Publication No. WO 2008/108343, and the like. Further, the water-soluble polyvalent metal cation-containing compound can also be used as the "another surface crosslinking agent" of the present invention.

(Surfactant)

A polyacrylic acid (salt)-based water-absorbent resin of the present invention can contain a surfactant which is preferably mixed in any of the steps included in the production method in accordance with the present invention.

By coating a surface of a water-absorbing resin of the present invention with a surfactant, it is possible to obtain a water-absorbing agent having a high water absorbing speed and high liquid permeability. Note that the surfactant as used in the present invention is exemplified by but not particularly limited to surfactants disclosed in International Publication No. WO 97/017397 and the specification of U.S. Pat. No. 6,107,358, i.e., a nonionic surfactant, an anionic surfactant, a cationic surfactant, an amphoteric surfactant, a silicone-based surfactant, and the like. These surfactants can be polymerizable or reactive with an acrylic acid (salt)-based monomer or a water-absorbing resin. As specific surfactants, compounds disclosed in Patent Literatures 45 and 46 are employed.

A type and a used amount of a surfactant to be used are appropriately determined. The surfactant of the present invention is preferably used so that a water-absorbing agent has a surface tension that falls within a range described in the specification of U.S. Patent No. 2006/204755. Specifically, the surfactant of the present invention is used in an amount preferably of 0 part by weight to 0.5 parts by weight, more preferably of 0.00001 parts by weight to 0.1 parts by weight, and even more preferably of 0.001 parts by weight to 0.05 parts by weight, based on a water-absorbing resin. Of the surfactants mentioned above, an anionic surfactant, a nonionic surfactant, or a silicone-based surfactant is more preferably used, and a nonionic surfactant or a silicone-based surfactant is even more preferably used.

(Step of Adding Another Additive)

The present step, which is a step of adding another additive so as to provide a water-absorbing resin and water-absorbing resin particles with various functions, consists of one step or two or more steps. The another additive is exemplified by not only the liquid permeability improving agent and the surfactant, which are described earlier, but also a deodorant, a perfume, an antimicrobial agent, a foaming agent, a chelating agent, an anti-coloring agent, a pigment, a dye, a fertilizer, an oxidant, a reducing agent, and the like. Such an additive is used in an amount of less than 10 weight %, more preferably of less than 5 weight %, and even more preferably of less than 1 weight %, based on the water-absorbing resin and the water-absorbing resin particles. Further, such an additive can be added simultaneously with or separately from the surface crosslinking step. In addition, water can be added, or any of the above additives can be added as an aqueous solution.

[3] Physical Property of Polyacrylic Acid (Salt)-Based Water-Absorbing Agent (3-1) AAP (Fluid Retention Capacity Under Load)

In a case where surface crosslinking after the polymerization is taken as an example of means for achieving the following AAP, the water-absorbing agent in accordance with the present invention has a fluid retention capacity (AAP) of at least 20 g/g, more preferably of at least 23 g/g, and even more preferably of at least 23.5 g/g, based on a 0.9 weight % aqueous sodium chloride solution under a load of 4.8 kPa. Note that though the water-absorbing agent which has a higher AAP is more preferable, from the viewpoint of a balance between the AAP and other physical properties (e.g., SFC), the water-absorbing agent of the present invention has an AAP whose upper limit is preferably not more than 40 g/g, more preferably not more than 35 g/g, and even more preferably not more than 30 g/g. Note that an AAP of a water-absorbing agent can be controlled by surface crosslinking, a CRC, and a liquid permeability improving agent.

(3-2) PUP Under 0.58 Psi (Fluid Retention Capacity Under Load)

In a case where surface crosslinking after the polymerization is taken as an example of means for achieving the following PUP, the water-absorbing agent in accordance with the present invention has a fluid retention capacity (PUP) of not less than 30 g/g, more preferably of not less than 31 g/g, and even more preferably of not less than 32 g/g, based on an aqueous artificial urine solution under a load of 4.12 kPa. Note that though the water-absorbing agent which has a higher PUP is more preferable, from the viewpoint of a balance between the PUP and other physical properties (e.g., SFC), the water-absorbing agent of the present invention has a PUP whose upper limit is preferably not more than 50 g/g, more preferably not more than 45 g/g, and even more preferably not more than 40 g/g. Note that a PUP of a water-absorbing agent can be controlled by surface crosslinking, a CRC, and a liquid permeability improving agent.

(3-3) CRC (Fluid Retention Capacity without Load)

The water-absorbing agent in accordance with the present invention has a fluid retention capacity without load (CRC) preferably of not less than 20 g/g, more preferably of not less than 23 g/g, even more preferably of not less than 25 g/g, especially even more preferably of not less than 26 g/g, and most preferably of not less than 28 g/g. The water-absorbing agent which has a low fluid retention capacity without load absorbs water with lower efficiency when used in sanitary products such as a disposable diaper. Note that though the water-absorbing agent which has a higher CRC is more preferable, from the viewpoint of a balance between the CRC and other properties (e.g., SFC), the water-absorbing agent has a CRC whose upper limit is preferably not more than 60 g/g, more preferably not more than 50 g/g, and even more preferably not more than 35 g/g. Note that a CRC of a water-absorbing agent can be controlled by a polymerization step and/or a surface crosslinking step.

(3-4) SFC (Saline Flow Conductivity)

Though depending on a water-absorbing agent content (weight %) in a sanitary product, the saline flow conductivity (SFC) is required to be higher in numerical value as the water-absorbing agent content increases.

From the viewpoint of a balance between the SFC and other properties (e.g., CRC), the SFC has an upper limit preferably of approximately not more than $300 \times 10^{-7} \cdot cm^3 \cdot s \cdot g^{-1}$. Note that an SFC can be controlled by the particle size (described earlier) and a CRC (the polymerization step and/or the surface crosslinking step).

In a case where the polymerization and surface crosslinking after control of a size of water-absorbing resin particles are taken as an example of means for achieving the following SFC, the water-absorbing agent in accordance with the present invention has a 0.69 weight % saline flow conductivity (SFC), which is permeability of a liquid under load, of at least $10 \times 10^{-7} \cdot cm^3 \cdot s \cdot g^{-1}$, more preferably of at least $15\times10^{-7}\cdot cm^3\cdot s\cdot g^{-1}$, even more preferably of at least $20\times 10^{-7}\cdot cm^3\cdot s\cdot g^{-1}$, still further more preferably of at least $30\times10^{-7}\cdot cm^3\cdot s\cdot g^{-1}$, especially even more preferably of at least $50\times10^{-7}\cdot cm^3\cdot s\cdot g^{-1}$, and most preferably of at least $70\times10^{-7}\cdot cm^3\cdot s\cdot g^{-1}$.

(3-5) Salt Tolerance Index

Water-absorbing resin particles and a water-absorbing agent each of which is to be obtained in the present invention have a Salt Tolerance Index which is represented by Formula 1 below, the Salt Tolerance Index satisfying Formula 2 below and being preferably 5.7 or less, more preferably 5.6 or less, and even more preferably 5.5 or less. The Salt Tolerance Index normally has a lower limit preferably of at least 1.0, more preferably of at least 2.0, even more preferably of at least 3.0, especially even more preferably of at least 4.0, and most preferably of at least 5.0. A typical range of the Salt Tolerance Index, which typical range is appropriately selectable within a range of the above upper limit to the above lower limit, is preferably from 1.0 to 5.7, preferably from 2.0 to 5.7, from 3.0 to 5.7, from 4.0 to 5.7, and from 5.0 to 5.7 in this order, more preferably from 5.0 to 5.6, and even more preferably from 5.0 to 5.5.

The Salt Tolerance Index which satisfies Formula 2 allows the water-absorbing agent not only to have excellent salt resistance but also to have high liquid permeability while maintaining a high water absorbing speed.

$$\text{Salt Tolerance Index}=(CRCdw)/(CRCs) \quad \text{(Formula 1)}$$

where CRCdw is a centrifuge retention capacity (g/g) for deionized water (dw), and CRCs is a centrifuge retention capacity (g/g) for a 0.9 weight % saline, $$\text{Salt Tolerance Index}\le 0.49\times CRCs-7.47 \quad \text{(Formula 2)}$$

(3-6) FSR (Free Swell Rate)

In a case where the polymerization (foaming polymerization) is taken as an example of means for achieving the following FSR, 1 g of the water-absorbing agent of the present invention has a Free Swell Rate (FSR) of at least 0.28 g/g/sec, more preferably of at least 0.30 g/g/sec, and even more preferably of at least 0.35 g/g/sec, based on 20 g of a physiological saline solution. The Free Swell Rate (FSR) has an upper limit preferably of at least 1.0 g/g/s and more preferably of at least 0.50 g/g/s. A typical range of the FSR, which typical range is appropriately selectable within a range of the above upper limit to the above lower limit, is preferably from 0.28 g/g/s to 1.0 g/g/s, more preferably from 0.30 g/g/s to 0.50 g/g/s, and even more preferably from 0.35 g/g/s to 0.5 g/g/s. Further, any range such as a range of 0.30 g/g/s to 1.0 g/g/s, a range of 0.35 g/g/s to 1.0 g/g/s, or the like can also be selected as the typical range. Note that a method for measuring an FSR is defined by the pamphlet of International Publication No. WO 2009/016055.

(3-7) Bulk Specific Gravity

The water-absorbing agent in accordance with the present invention has a bulk specific gravity of 0.55 g/cm$^3$ to 0.70 g/cm$^3$, more preferably of 0.57 g/cm$^3$ to 0.68 g/cm$^3$, and even more preferably of 0.59 g/cm$^3$ to 0.66 g/cm$^3$. In the present invention, the bulk specific gravity of the water-absorbing agent is preferably controlled so as to fall within the above range. Note that a bulk specific gravity of a water-absorbing agent can be controlled by, for example, a pulverization step and/or a classification step.

(3-8) Absorption Time (Vortex)

The water-absorbing agent in accordance with the present invention has an Absorption Time of 42 seconds or less, preferably of 36 seconds or less, more preferably of 33 seconds or less, and even more preferably of 30 seconds or less. Though a shorter Absorption Time is preferable as a lower limit, the Absorption Time normally has a lower limit preferably of not shorter than 1 second and more preferably of not shorter than 5 seconds. A typical range of the Absorption Time, which typical range is appropriately selectable within a range of the above upper limit to the lower limit, is preferably from 1 to 42 seconds, more preferably from 1 to 36 seconds, even more preferably from 1 to 30 seconds, and especially even more preferably from 5 to 30 seconds.

(3-9) Particle Size Distribution and Additive for Functionalization

The water-absorbing resin, the water-absorbing resin particles, and the water-absorbing agent each of which is to be obtained in the present invention are not particularly limited in particle diameter and particle size distribution. Note, however, that it is preferable to obtain, by particle sizing after addition and mixing of the last organic surface cross-linking agent, particles of less than 1 mm and further a water-absorbing resin or a water-absorbing agent having the particle diameter below. In a case where a water-absorbing resin or a water-absorbing agent which contains, in a large number, particles of not less than 1 mm, especially of not less than 850 µm, particularly in a case where a water-absorbing resin, for example which contains such coarse particles is used in each of a thin sanitary product and a thin absorbent article, those coarse particles not only cause discomfort to a wearer of each of the thin sanitary product and the thin absorbent article but also damages, by abrasion, a water impermeable material, i.e., a so-called back sheet of which the absorbent article is made, and consequently may cause leakage of, for example, urine in actual use of the thin sanitary product and the thin absorbent article. Thus, a water-absorbing resin or a water-absorbing agent which contains such coarse particles in a large number is not preferable. In view of the above, a smaller number of particles of not less than 850 µm are desirable, and particles of not less than 850 µm are contained in an amount preferably of 0 weight to 5 weight, more preferably of 0 weight % to 3 weight %, even more preferably of 0 weight % to 1 weight %, and especially even more preferably of substantially 0 weight %.

Meanwhile, the water-absorbing resin, the water-absorbing resin particles, and the water-absorbing agent of the present invention each contain, in an amount preferably of 0 weight % to 3.0 weight %, more preferably of 0 weight % to 2.0 weight %, and even more preferably of 0 weight % to 1.5 weight %, a fine powder having a particle diameter of less than 150 µm.

Furthermore, while maintaining (i) the above range in which the coarse particles are contained in each of the water-absorbing resin, the water-absorbing resin particles, and the water-absorbing agent of the present invention and (ii) the above range in which the fine powder is contained in each of the water-absorbing resin, the water-absorbing resin particles, and the water-absorbing agent of the present invention, the water-absorbing resin, the water-absorbing resin particles, and the water-absorbing agent of the present invention each have a particle diameter distribution (content) of particles of 150 µm to 850 µm of preferably not less than 95 weight % (upper limit: 100 weight %), more preferably not less than 98 weight %, even more preferably not less than 99 weight %, and most preferably substantially 100 weight %.

The water-absorbing agent to be obtained as an end product through the above steps in the present invention has a weight average particle diameter (D50) (defined by standard sieve classification of water-absorbing resin) preferably of not less than 200 μm and not more than 600 μm. In order to improve performance, the water-absorbing resin has a weight average particle diameter (D50) more preferably of 200 μm to 550 μm, even more preferably of 250 μm to 500 μm, and most preferably of 350 μm to 450 μm. Further, particles having a particle diameter of less than 300 μm are contained in the water-absorbing agent in an amount preferably of not less than 10 weight %, more preferably of 10 weight % to 50 weight %, and even more preferably of 10 weight % to 30 weight %.

The water-absorbing agent has a moisture content (rate of reduction in weight at 180° C. in three hours) preferably of 0 weight % to 15 weight %, more preferably of 0.1 weight % to 10 weight %, and even more preferably of 0.5 weight % to 8 weight %.

A particle size of the water-absorbing agent in accordance with the present invention can be appropriately controlled by, for example, pulverization, classification, and/or granulation.

As described earlier, a polyacrylic acid (salt)-based water-absorbing agent of the present invention, whose surface and its vicinity are crosslinked by an organic surface crosslinking agent, characterized by satisfying the following (A)-(D):

(A) Free Swell Rate (FSR) of at least 0.28 g/g/s, or Absorption Time (Vortex) of 42 seconds or less;

(B) Absorption Against Pressure (AAP) of at least 20 g/g;

(C) Salt Tolerance Index represented by the following Formula 1 satisfying the following Formula 2:

$$\text{Salt Tolerance Index}=(CRCdw)/(CRCs) \quad \text{(Formula 1)}$$

where CRCdw is a centrifuge retention capacity (unit; g/g) for deionized water (dw), and CRCs is a centrifuge retention capacity (unit; g/g) for a 0.9 weight % saline, $$\text{Salt Tolerance Index} \leq 0.49 \times CRCs - 7.47 \quad \text{(Formula 2)};$$

and (D) Bulk Specific Gravity of 0.55 to 0.70 g/cm³.

A method for producing a polyacrylic acid (salt)-based water-absorbing agent of the present invention, includes heat treating a mixture containing water, a surface crosslinking agent and a water-absorbing resin powder, wherein the water-absorbing resin powder is heat treated for at least five minutes from a start of raising a temperature with a gas density of a surface crosslinking agent C2 compound and/or a surface crosslinking agent C3 compound being at least 0.01 g/L.

Where the surface crosslinking agent C2 compound is a compound, of which longest carbon chain has 2 carbons, containing a total number of carbons of 3 or less, with either one of an oxygen atom or a nitrogen atom being bonded to each of carbon atoms at both ends of the carbon chain; and the surface crosslinking agent C3 compound is a compound, of which longest carbon chain has 3 carbons, containing a total number of carbons of 4 or less, with either one of an oxygen atom or a nitrogen atom being bonded to each of different carbon atoms on the carbon chain; and the gas density is a weight of the surface crosslinking agent C2 compound or the surface crosslinking agent C3 compound that is contained per unit volume of a non-condensable gas.

[4] Use Etc. of Polyacrylic Acid (Salt)-Based Water-Absorbing Agent

In a case where the numerical values mentioned above fall outside the ranges mentioned above, it may be impossible to obtain a balanced water-absorbing agent having excellent liquid permeability while maintaining a desired fluid retention capacity. In particular, particles having a particle diameter of less than 150 μm are preferably as few as possible. This is because such particles may not only cause a deterioration in liquid permeability but also cause an adverse effect due to, for example, dust generated in an operational environment for production of an absorbent article of which a water-absorbing agent is made.

The water-absorbing agent of the present invention can be provided with or improve in function by containing not only surface-crosslinked water-absorbing resin particles but also preferably a liquid permeability improving agent or an additive selected from water-insoluble fine particulate compounds and polyvalent cationic compounds, and by further containing other additives such as a deodorant, a perfume, an antimicrobial agent, a foaming agent, a chelating agent, a surfactant, an anti-coloring agent, a pigment, a dye, a fertilizer, an oxidant, and a reducing agent. Such an additive(s) is/are used in an amount of less than 10 weight %, preferably less than 5 weight %, and more preferably less than 1 weight %, based on a total amount of water-absorbing resin particles and a water-soluble polyvalent metal cation-containing compound.

The water-absorbing agent of the present invention is used in sanitary products such as disposable diapers, sanitary napkins, incontinence pads, and medical pads. Such a sanitary product in which the water-absorbing resin of the present invention is used is preferably used by including (a) a liquid permeable top sheet provided so as to adjoin a body of a wearer, (b) a liquid impermeable back sheet provided so as to be away from the body of the wearer and adjoin clothing of the user, and (c) an absorbent body provided between the top sheet and the back sheet. The absorbent body can also have two or more layers and/or be used in combination with, for example, a pulp layer.

In a case where the water-absorbing agent of the present invention is used in a sanitary product, a gel having absorbed liquid is less likely to cause so-called gel blocking. This prevents a space between respective gel particles from being blocked by gels that are in close contact with each other. Thus, even in a case where the water-absorbing agent is used at a high concentration in an absorbent body such as a disposable diaper, urine and a bodily fluid discharged for the second or later time can be diffused throughout an inside of the absorbent body without being stuck on a surface of the absorbent body. This allows the urine and the bodily fluid to be distributed over the water-absorbing agent inside the absorbent body.

EXAMPLES

The following description discusses the present invention with reference to Examples, Comparative Examples, and Reference Examples. Note, however, that the present invention should not be interpreted by being limited by, for example, these examples. Physical properties described in the Claims and the Examples of this specification were calculated under conditions of a room temperature of 23±2° C. and a humidity of 50±10 RH % by measurement methods described in Sections (5-1) to (5-8) below. Note that unless otherwise specified, each step in each example was carried out under substantially atmospheric pressure (atmospheric pressure ±5%, more preferably ±1%), and was carried out without changing a pressure by intentionally increasing or decreasing the pressure in an identical step. Note also that though Sections (5-1) to (5-8) below discuss measurement of physical properties of a water-absorbing resin, in a case where a water-absorbing resin powder, water-absorbing resin particles, or a water-absorbing agent is to be measured, those physical properties are applied to the water-absorbing resin powder, the water-absorbing resin particles, or the water-absorbing agent by reading the water-absorbing agent as the water-absorbing resin powder, the water-absorbing resin particles, or the water-absorbing agent.

(5-1) Fluid Retention Capacity without Load (CRC)

In accordance with the method described in ERT441.2-0.2, 0.200 g of a water-absorbing resin was allowed to freely swell in a large excess of a 0.90 weight % aqueous sodium chloride solution (also referred to as "physiological saline") without load for 30 minutes. Then, a fluid retention capacity (CRC) after draining of water by centrifugal separation was measured.

(5-2) Fluid Retention Capacity Under Load (AAP/Absorbency Against Pressure)

In accordance with the fluid retention capacity under load evaluation method described in the publication of EDANA (European Disposables and Nonwovens Association) and the method described in ERT442.2-02, measurement was carried out by allowing 0.900 g of a water-absorbing resin to freely swell in a 0.9 weight % aqueous sodium chloride solution for 1 hour. Note, however, that in the present invention, a fluid retention capacity under load (g/g) of a water-absorbing resin was calculated by replacing the load of each of the above methods with a load of 4.83 kPa (approximately 0.7 psi).

(5-3) Liquid Permeability (SFC)

An SFC was measured by a method, which is a well-known measurement method and is disclosed in the pamphlet of International Publication No. WO 95/26209.

(5-4) FSR (Free Swell Rate)

1.00 g of a water-absorbing resin was placed in a 25 ml glass beaker (32 mm to 34 mm in diameter and 50 mm in height). The water-absorbing resin was placed in the beaker in such a manner that a top surface of the water-absorbing resin in the beaker was level (if necessary, a surface of the water-absorbing resin can be made level by taking action, e.g., by tapping the beaker carefully).

Then, 20 g of a 0.90 weight % aqueous sodium chloride solution adjusted to have a temperature of 23° C.±0.2° C. was weighed in a 50 ml cylindrical glass beaker (32 mm in internal diameter and 52 mm in height), and a total weight (unit; g) of the aqueous sodium chloride solution and the glass beaker (this weight is referred to as "weight W6") was measured. The weighed sodium chloride solution was poured carefully and swiftly into the 25 ml beaker in which the water-absorbing resin was placed. Time measurement was started upon contact between the poured aqueous sodium chloride solution and the water-absorbing resin. Then, a top surface of the aqueous sodium chloride solution in the beaker into which the aqueous sodium chloride solution had been poured was visually observed at an angle of approximately 20°. In this case, when the top surface, which had been a surface of the aqueous sodium chloride solution, was replaced with a surface of the water-absorbing resin which surface had absorbed the aqueous sodium chloride solution by absorption of the aqueous sodium chloride solution by the water-absorbing resin, the time measurement was ended (unit; second/time) (this is referred to as "ts").

Next, a weight (unit; g) of the 50 ml beaker into which the aqueous sodium chloride solution had been poured (this weight is referred to as "weight W7") was measured. A weight of the poured aqueous sodium chloride solution (this weight is referred to as "weight W8") and FSR were calculated based on the following Formula 3 and the following Formula 4, respectively:

$$W8(g)=W6-W7 \quad \text{(Formula 3)}$$

$$FSR(g/g/s)=W8/(ts(\text{second}) \times \text{weight}(g) \text{ of water-absorbing resin}) \quad \text{(Formula 4)}$$

(5-5) Bulk Specific Gravity

A bulk specific gravity was measured by use of a bulk specific gravity measuring device (manufactured by Kuramochi Scientific Instrument Seisakusho) in conformity with JIS K 3362. After 100.0 g of a water-absorbing resin, which was sufficiently stirred so as to prevent deviation due to a difference in particle size, was placed in a funnel whose damper was closed, the damper was opened quickly so that the water-absorbing resin was dropped into a receiver having an internal capacity of 100 ml. Note that a weight (unit; g) of the receiver (this weight is referred to as "weight W9") was weighed in advance.

After a part of the water-absorbing resin, which part was protruding on the receiver, was removed by use of a glass rod, a weight (unit; g) of the receiver containing the water-absorbing resin (this weight is referred to as "weight W10") was accurately measured to the unit of 0.1 g, and a bulk specific gravity was calculated based on the following Formula 5:

$$\text{Bulk specific gravity}(g/cm^3)=(W10-W9)/100 \quad \text{(Formula 5)}$$

Note that the measurement was carried out at an ambient temperature of 24.2° C. and at a relative humidity of 43% RH.

(5-6) Particle Size (Particle Size Distribution, Weight Average Particle Diameter (D50), Logarithmic Standard Deviation ($\sigma\zeta$) of Particle Size Distribution)

A particle size (particle size distribution, weight average particle diameter (D50), logarithmic standard deviation ($\sigma\zeta$) of particle size distribution) of a water-absorbing resin of the present invention was measured in conformity with "(3) Mass-Average Particle Diameter (D50) and Logarithmic Standard Deviation (o) of Particle Diameter Distribution" described in columns 27 and 28 of the specification of the U.S. Pat. No. 7,638,570.

(5-7) Solid Content

A solid content of the water-absorbing resin of the present invention was calculated based on the following Formula 6:

$$\text{Solid content(weight \%)}=100-\text{moisture content} \quad \text{(Formula 6)}$$

Note that the moisture content in Formula (6) was measured in conformity with ENADA method (ERT430.2-02) by replacing the sample amount and the drying temperature of the ENADA method with 1.0 g and 180° C., respectively.

(5-8) Vortex (Absorption Time)

A solution in which 0.02 parts by weight of Food Blue No. 1, which is a food additive, was added to 1000 parts by weight of a 0.90 weight % aqueous sodium chloride solution (physiological saline) prepared in advance was prepared and adjusted to have a liquid temperature of 30° C.(±0.5° C.). In a 100 ml cylindrical beaker (51 mm in internal diameter and 72 mm in height), 50 ml of the solution was weighed. Then, 2.0 g of a water-absorbing resin powder obtained in Examples or Comparative Examples (described later) was introduced into the solution which was being stirred at 600 rpm by use of a cylindrical stirring bar (40 mm in length and 8 mm in thickness) coated with Teflon (Registered Trademark). A absorption time was thus measured.

In conformity with a reference described in "koukyusui-seijyushi-no kyushusokudo shiken houhou kaisetsu (Explanation of Method for Testing Absorption Speed of Superabsorbent Resin)" of JIS K 7224 (1996), an end point of the absorption time was measured assuming that a time between absorption of a physiological saline by a water-absorbing resin powder and coating of the cylindrical stirring bar with the water-absorbing resin powder was a absorption time (unit; second) by Vortex method.

Reference Example 1

In the present Reference Example 1, a water-absorbing resin powder (A) that was particulate and had not been surface-crosslinked was obtained by carrying out polymerization, gel grinding, drying, pulverization, and classification with reference to Example 3 of the pamphlet of International Publication No. WO 2010/095427. This is specifically described below.

A solution (A) was prepared by placing and mixing, in a 1 L container made of polypropylene, 421.7 g of acrylic acid, 2.754 g of polyethylene glycol diacrylate (molecular weight: 523) as an internal crosslinking agent, 113.43 g of a 0.1 weight % aqueous diethylenetriamine pentaacetic acid trisodium solution as a chelating agent, 140.4 g of a 48.5 weight % aqueous sodium hydroxide solution, and 292.3 g of deionized water (ion exchanged water). While the solution (A) was being adjusted to have a temperature of 40° C., microbubbles were introduced into the solution (A) by use of a microbubble generator (manufactured by AURA TEC CO., LTD.; model: OM4-GP-040) under an absolute pressure of 0.25 MPa to 0.30 MPa for 1 minute assuming that nitrogen gas was introduced gas.

Next, 211.9 g of a 48.5 weight % aqueous sodium hydroxide solution adjusted to have a temperature of 40° C. was quickly added to the solution (A) into which the microbubbles had been introduced, and a resultant solution was mixed, so that an aqueous monomer solution (A) was obtained. In this case, the aqueous monomer solution (A) had a temperature of 85° C.

Subsequently, to the aqueous monomer solution (A), which had kaolin turbidity of 530 mg/L at a point in time at which the temperature of the aqueous monomer solution (A) decreased to 82° C. and which was made whitish, 17.55 g of a 4 weight % aqueous sodium persulfate solution was added while being stirred, and thereafter a resultant mixture was immediately poured, in an atmospheric air open system, into a stainless-steel vat container (having a bottom surface of 340 mm×340 mm, a height of 25 mm, and an inner surface coated with Teflon (Registered Trademark)) whose surface temperature was increased to 80° C. by use of a hot plate (manufactured by Iuchi Seieido Co., Ltd.; NEO HOTPLATE HI-1000).

Polymerization started immediately after the aqueous monomer solution (A) was poured into the vat. The polymerization progressed while water vapor was being generated and swelling and foaming was vertically and horizontally occurring, and then the aqueous monomer solution (A) shrunk to a size which was slightly larger than that of the stainless-steel vat container. The swelling and shrinking ended within approximately 1 minute. After 3 minutes elapsed, a hydrogel-forming crosslinked polymer (hydrogel) (A) obtained was taken out. Note that this series of operations was carried out in an atmospheric air open system.

The hydrogel (A) obtained by the above operations was subjected to gel grinding by use of a meat chopper (manufactured by Iizuka Kogyo Co., Ltd., MEAT-CHOPPER TYPE: 12VR-400KSOX, die pore diameter: 6.4 mm, the number of pores: 38, die thickness: 8 mm), so that a particulate hydrogel (A) was obtained. In this case, an amount of input of the hydrogel (A) was approximately 350 g/min, and deionized water which had been adjusted to have a temperature of 90° C. was added at 80 g/min simultaneously with the input of the hydrogel (A).

The hydrogel (A) grain-refined and obtained by the gel grinding was spread over and placed on a woven stainless-steel wire having a mesh size of 850 μm, and was dried at 180° C. for 30 minutes by letting hot air through. Next, a dried polymer (A) obtained by the drying was pulverized by use of a roll mill (manufactured by Inoguchi Giken Ltd., WML-type roll crusher) and then classified by use of a JIS standard sieve having a mesh size of 850 μm and a JIS standard sieve having a mesh size of 45 μm.

By the above operations, a water-absorbing resin powder (A) was obtained which was ground to have an uneven shape and which had a solid content of 97 weight %, a weight average particle diameter (D50) of 446 μm, and a particle size distribution having a logarithmic standard deviation (σζ) of 0.39. Physical properties of the obtained water-absorbing resin powder (A) are shown in Table 1.

Comparative Example 1

The water-absorbing resin powder (A) obtained in Reference Example 1 was used to carry out surface crosslinking with reference to Example 9 of the pamphlet of International Publication No. WO 2010/095427. This is specifically described below.

Into 100 parts by weight of the water-absorbing resin powder (A) obtained in Reference Example 1, a surface crosslinking agent solution containing 0.48 parts by weight of ethylene glycol, 0.75 parts by weight of propylene glycol, and 4.0 parts by weight of deionized water was uniformly sprayed and mixed.

A mixture (A) obtained by the above mixing operation was surface-crosslinked by being heat-treated by use of a hot air dryer (temperature: 180° C.) for 40 minutes.

The mixture (A), which had been heat-treated, was pulverized until the mixture (A) passed through a JIS standard sieve having a mesh size of 850 μm, so that comparative water-absorbing resin particles (1) that had been surface-crosslinked were obtained.

As to this surface crosslinking condition, a change in concentration (gas density) of the surface crosslinking agent in the hot air dryer was analyzed by collecting gas in the hot air dryer per minute from the start of the surface crosslinking. As a result, ethylene glycol had a gas density of 0.0054 g/L after 1 minute; 0.0092 g/L after 2 minutes; 0.0068 g/L after 3 minutes; and 0.0047 g/L after 4 or more minutes, from the start of an increase in temperature of the water-absorbing resin powder (A).

Meanwhile, propylene glycol had a gas density of 0.0081 g/L after 1 minute; 0.011 g/L after 2 minutes; 0.0076 g/L after 3 minutes; and 0.0053 g/L after 4 or more minutes, from the start of the increase in temperature of the water-absorbing resin powder (A).

To 100 parts by weight of the comparative water-absorbing resin particles (1) obtained by the above operations, a mixed solution containing 0.80 parts by weight of a 27 weight % aqueous aluminum sulfate solution (8 weight % in terms of aluminum oxide) as a water-soluble polyvalent metal cation-containing compound, 0.134 parts by weight of a 60 weight % aqueous sodium lactate solution as α-hydroxycarboxylic acid, and 0.016 parts by weight of propylene glycol was added, and then a resultant mixture was dried at 60° C. for 1 hour under a windless condition.

Then, after the drying, resultant particles were allowed to pass through the JIS standard sieve having a mesh size of 850 µm, so that a comparative water-absorbing agent (1) was obtained. Physical properties of the obtained comparative water-absorbing agent (1) are shown in Table 2.

Example 1

Operations similar to those carried out in Comparative Example 1 were carried out except that a heated gaseous surface crosslinking agent was externally introduced so that ethylene glycol and propylene glycol in a hot air dryer for carrying out a heat treatment each had a gas density of 0.01 g/L at all times for not shorter than five minutes of the start of surface crosslinking, so that a water-absorbing agent (1) was obtained. Physical properties of the obtained water-absorbing agent (1) are shown in Table 2.

Reference Example 2

In the present Reference Example 2, a water-absorbing resin powder (B) that was particulate and had not been surface-crosslinked was obtained by carrying out polymerization, gel grinding, drying, pulverization, and classification with reference to Example 2 of the pamphlet of International Publication No. WO 2011/078298. This is specifically described below.

A solution (B) was prepared by placing and mixing, in a 2 L container made of polypropylene, 351.6 g of acrylic acid, 2.17 g of polyethylene glycol diacrylate (molecular weight: 523) as an internal crosslinking agent, 94.6 g of a 0.1 weight % aqueous diethylenetriamine pentaacetic acid trisodium solution as a chelating agent, 144.9 g of a 48.5 weight % aqueous sodium hydroxide solution, 6.45 g of a 1.0 weight % aqueous polyoxyethylene (20) sorbitane monostearate (manufactured by Kao Corporation) solution as a surfactant, and 236.0 g of deionized water (ion exchanged water). A temperature of the solution (B) rose to 65° C. by heat of a first stage neutralization immediately after the preparation. The solution (B) containing the surfactant was made whitish by introduction thereinto of extremely tiny gas bubbles due to a decrease in gas solubility caused by the temperature rise.

Next, the solution (B) was cooled while being stirred. At a point in time at which the temperature of the solution reached 53° C., 148.9 g of a 48.5 weight % aqueous sodium hydroxide solution which had been adjusted to have a temperature of 30° C. was added to and mixed with the solution, so that an aqueous monomer solution (B) was prepared. In this case, a temperature of the aqueous monomer solution (B) rose to 83.5° C. by heat of a second stage neutralization immediately after the preparation. The aqueous monomer solution (B) containing the surfactant was made whitish by introduction thereinto of extremely tiny gas bubbles due to a decrease in gas solubility caused by the temperature rise.

Subsequently, at a point in time at which the temperature of the aqueous monomer solution (B) decreased to 83° C., 15.3 g of a 3.8 weight % aqueous sodium persulfate solution was added, while being stirred, to the aqueous monomer solution (B), and thereafter a resultant mixture was immediately poured into a stainless-steel vat container (having a bottom surface of 340 mm×340 mm, a height of 25 mm, and an inner surface coated with Teflon (Registered Trademark)) in an atmospheric air open system. Note that the vat container was heated by use of a hot plate (manufactured by Iuchi Seieido Co., Ltd.; NEO HOTPLATE HI-1000) until a surface temperature of the vat container was increased to 40° C. Note also that the aqueous monomer solution (B) to which the aqueous sodium persulfate solution had not been added had a dissolved oxygen content of 6.53 ml/L.

A polymerization reaction started after the elapse of seconds from the pouring of the aqueous monomer solution (B) into the vat container. The polymerization reaction progressed while water vapor was being generated and swelling and foaming was vertically and horizontally occurring, and then the aqueous monomer solution (B) shrunk to a size which was slightly larger than that of the vat container. The swelling and shrinking ended within approximately 1 minute. After 3 minutes elapsed from the start of the polymerization reaction, a hydrogel-forming crosslinked polymer (hydrogel) (B) obtained was taken out. Note that this series of operations was carried out in an atmospheric air open system, and a peak temperature during polymerization was 108° C.

The hydrogel (B) obtained by the above operations was subjected to gel grinding by use of a meat chopper (manufactured by Iizuka Kogyo Co., Ltd., MEAT-CHOPPER TYPE: 12VR-400KSOX, die pore diameter: 6.4 mm, the number of pores: 38, die thickness: 8 mm), so that a particulate hydrogel (B) was obtained. In this case, an amount of input of the hydrogel (B) was approximately 350 g/min, and deionized water which had been adjusted to have a temperature of 90° C. was added at 80 g/min simultaneously with the input of the hydrogel (B).

The hydrogel (B) grain-refined and obtained by the gel grinding was spread over and placed on a woven stainless-steel wire having a mesh size of 850 µm, and was dried at 180° C. for 30 minutes by letting hot air through. Next, a dried polymer (B) obtained by the drying was pulverized by use of a roll mill (manufactured by Inoguchi Giken Ltd., WML-type roll crusher) and then classified by use of a JIS standard sieve having a mesh size of 850 µm and a JIS standard sieve having a mesh size of 45 µm.

By the above operations, a water-absorbing resin powder (B) was obtained which was ground to have an uneven shape and which had a solid content of 97 weight %, a weight average particle diameter (D50) of 460 µm, and a particle size distribution having a logarithmic standard deviation (σζ) of 0.40. Physical properties of the obtained water-absorbing resin powder (B) are shown in Table 1.

Comparative Example 2

The water-absorbing resin powder (B) obtained in Reference Example 2 was used to carry out surface crosslinking with reference to Example 12 of the pamphlet of International Publication No. WO 2011/078298. This is specifically described below.

Into 100 parts by weight of the water-absorbing resin powder (B) obtained in Reference Example 2, a surface crosslinking agent solution containing 0.48 parts by weight of 1,4-butanediol, 0.75 parts by weight of propylene glycol, 0.001 parts by weight of polyoxyethylene (20) sorbitane monostearate (manufactured by Kao Corporation) (10 ppm relative to the water-absorbing resin powder (B)), and 4.0 parts by weight of deionized water was uniformly sprayed and mixed.

A mixture (B) obtained by the above mixing operation was surface-crosslinked by being heat-treated by use of a hot air dryer (temperature: 180° C.) for 45 minutes.

The mixture (B), which had been heat-treated, was pulverized until the mixture (B) passed through a JIS standard sieve having a mesh size of 850 µm, so that comparative water-absorbing resin particles (2) that had been surface-crosslinked were obtained.

As to this surface crosslinking condition, a change in concentration of the surface crosslinking agent in the hot air dryer was analyzed by collecting gas in the hot air dryer per minute from the start of the surface crosslinking. As a result, 1,4-butandiol had a gas density of 0.0075 g/L after 1 minute; 0.01 g/L after 2 minutes; 0.0075 g/L after 3 minutes; and 0.005 g/L after 4 or more minutes, from the start of an increase in temperature of the water-absorbing resin powder (B).

Meanwhile, propylene glycol had a gas density of 0.085 g/L after 1 minute; 0.015 g/L after 2 minutes; 0.0085 g/L after 3 minutes; and 0.005 g/L after 4 or more minutes, from the start of the increase in temperature of the water-absorbing resin powder (B).

Further, under this surface crosslinking condition, a plurality of sets of comparative water-absorbing resin particles which sets had respective different water absorption capacities was obtained by changing, in a range of 20 minutes to 40 minutes, a time for which to carry out heating surface crosslinking. For these sets of comparative water-absorbing resin particles, an amount of a remaining and unreacted surface crosslinking agent was measured, and (i) amounts of decrease in fluid retention capacity caused by surface crosslinking when a surface crosslinking time is changed and (ii) residual ratios of a surface crosslinking agent were plotted so as to obtain graphs. The obtained graphs are shown in FIG. 1.

To 100 parts by weight of the comparative water-absorbing resin particles (2) obtained by the above operations, a mixed solution containing 0.80 parts by weight of a 27 weight % aqueous aluminum sulfate solution (8 weight % in terms of aluminum oxide) as a water-soluble polyvalent metal cation-containing compound, 0.134 parts by weight of a 60 weight % aqueous sodium lactate solution as α-hydroxycarboxylic acid, and 0.016 parts by weight of propylene glycol was added, and then a resultant mixture was dried at 60° C. for 1 hour under a windless condition.

Subsequently, after the drying, resultant particles were allowed to pass through the JIS standard sieve having a mesh size of 850 µm, so that a comparative water-absorbing agent (2) was obtained. Physical properties of the obtained comparative water-absorbing agent (2) are shown in Table 3.

Example 2

Operations similar to those carried out in Comparative Example 2 were carried out except that a heated gaseous surface crosslinking agent was externally introduced so that 1,4-butandiol and propylene glycol in a hot air dryer for carrying out a heat treatment each had a gas density of 0.0125 g/L at all times for not shorter than five minutes of the start of surface crosslinking, so that a water-absorbing agent (2) was obtained. Physical properties of the obtained water-absorbing agent (2) are shown in Table 3.

Further, under this surface crosslinking condition, a plurality of sets of water-absorbing resin particles which sets had respective different water absorption capacities was obtained by changing, in a range of 20 minutes to 40 minutes, a time for which to carry out heating surface crosslinking. For these sets of water-absorbing resin particles, an amount of a remaining and unreacted surface crosslinking agent was measured, and (i) amounts of decrease in fluid retention capacity caused by surface crosslinking when a surface crosslinking time is changed and (ii) residual ratios of a surface crosslinking agent were plotted so as to obtain graphs. The obtained graphs are shown in FIG. 1.

Reference Example 3

In the present Reference Example 3, a water-absorbing resin powder (C) that was particulate and had not been surface-crosslinked was obtained by carrying out polymerization, gel grinding, drying, pulverization, and classification with reference to Production Example 1 and Example 1 of the pamphlet of International Publication No. WO 2011/126079. This is specifically described below.

As an apparatus for producing a water-absorbing resin powder (C), there was prepared a continuous production apparatus including: a continuous polymerization device (stationary polymerization on a belt) for carrying out a polymerization step; a screw extruder for carrying out a gel grinding step; a continuous draft band dryer for carrying out a drying step; a three-stage roll mill for carrying out a pulverization step; JIS standard sieves for carrying out a classification step; and a transportation device for linking the above individual devices.

There was prepared an aqueous monomer solution (C) containing (i) 193.3 parts by weight of acrylic acid, (ii) 64.4 parts by weight of a 48 weight % aqueous sodium hydroxide solution, (iii) 1.26 parts by weight of polyethylene glycol diacrylate (average n number; 9), (iv) 52 parts by weight of a 0.1 weight % aqueous pentasodium ethylenediamine tetra (methylene phosphonate) solution, and (v) 134 parts by weight of deionized water.

Next, the aqueous monomer solution (C) which had been adjusted to have a temperature of 40° C. was continuously fed by use of a metering pump, and then 97.1 parts by weight of a 48 weight % aqueous sodium hydroxide solution was continuously mixed with the aqueous monomer solution (C) by line mixing. In this case, a temperature of the aqueous monomer solution (C) rose to 85° C. due to heat of neutralization.

Subsequently, 8.05 parts by weight of a 4 weight % aqueous sodium persulfate solution was continuously mixed with the aqueous monomer solution (C) by line mixing, and then a resultant mixture was continuously fed to a continuous polymerization device (stationary polymerization on a belt) having a planar polymerization belt with a dam at each end, so that the fed mixture had a thickness of approximately 7.5 mm. Thereafter, polymerization was continuously carried out, so that a hydrogel-forming crosslinked polymer (hereinafter referred to as a "hydrogel") (C) in a shape of a belt was obtained.

The obtained hydrogel (C) had a CRC of 28 g/g and a water soluble component of 4.0 weight %, the water soluble component having a weight average molecular weight of 218,377 Da.

The obtained hydrogel (C) was continuously cut at regular intervals in a direction perpendicular to a traveling direction of the belt so that a cut length was approximately 200 mm. Subsequently, while a supplying rate of the hydrogel (C) was set at 132,800 g/min, neither water nor water vapor was supplied, and a rotation rate of a screw shaft was 115 rpm, the hydrogel (C) was subjected to gel grinding by use of the screw extruder (meat chopper) having a porous plate provided at an end part thereof and having a diameter of 340 mm, a pore diameter of 22 mm, 105 pores, an aperture ratio of 52%, a thickness of 20 mm, and a diameter of the screw shaft of 152 mm. In this case, gel grinding energy (GGE) was 27.8 J/g. Note that a temperature of the hydrogel (C)

before gel grinding was 90° C., and a temperature of the hydrogel (C) after gel grinding (hereinafter referred to as a "ground gel") was 110° C.

The obtained ground gel (C) had a weight average particle diameter (D50) of 750 μm, a particle size distribution having a logarithmic standard deviation (σζ) of 0.79, a water soluble component of 4.4 weight %, and a solid content was of 50.8 weight %, the water soluble component having a weight average molecular weight of 253,596 Da.

Next, the ground gel (C) was introduced into the continuous draft band dryer within 1 minute after gel grinding and dried at 185° C. for 30 minutes, so that a dried polymer (C) was obtained. Note that the ground gel (C) to be introduced into the continuous draft band dryer had a temperature of 80° C.

Subsequently, a total amount of the dried polymer obtained by the drying step was pulverized (subjected to the pulverization step) by being continuously fed to the three-stage roll mill, and was classified (subjected to the classification step) by use of a JIS standard sieve having a mesh size of 710 μm and a JIS standard sieve having a mesh size of 175 μm, so that a water-absorbing resin powder (C) was obtained which was ground to have an uneven shape and had a weight average particle diameter (D50) of 350 μm and a particle size distribution having a logarithmic standard deviation (σζ) of 0.33. Physical properties of the obtained water-absorbing resin powder (C) are shown in Table 1.

Comparative Example 3

The water-absorbing resin powder (C) obtained in Reference Example 3 was used to carry out surface crosslinking with reference to Example 1 of the pamphlet of International Publication No. WO 2011/126079. This is specifically described below.

A surface crosslinking agent solution (covalent bonding surface crosslinking agent) containing 0.3 parts by weight of ethylene glycol, 0.6 parts by weight of propylene glycol, and 3.0 parts by weight of deionized water was uniformly mixed with 100 parts by weight of the water-absorbing resin powder (C) obtained in Reference Example 3, and then a resultant mixture was heat-treated at 208° C. for 40 minutes by use of a hot air dryer.

As to this surface crosslinking condition, a change in concentration of the surface crosslinking agent in the hot air dryer was analyzed by collecting gas in the hot air dryer per minute from the start of the surface crosslinking. As a result, ethylene glycol had a gas density of 0.0072 g/L after 1 minute; 0.011 g/L after 2 minutes; 0.0055 g/L after 3 minutes; and 0.0039 g/L after 4 or more minutes, from the start of an increase in temperature of the water-absorbing resin powder (C).

Meanwhile, propylene glycol had a gas density of 0.0083 g/L after 1 minute; 0.013 g/L after 2 minutes; 0.0069 g/L after 3 minutes; and 0.0049 g/L after 4 or more minutes, from the start of the increase in temperature of the water-absorbing resin powder (C).

Thereafter, resultant water-absorbing resin particles were cooled, and a mixed solution (ionic bonding surface crosslinking agent) containing 1.17 parts by weight of a 27.5 weight % aqueous aluminum sulfate solution (8 weight % in terms of aluminum oxide), 0.196 parts by weight of a 60 weight % aqueous sodium lactate solution, and 0.029 parts by weight of propylene glycol was uniformly mixed with the water-absorbing resin particles, and then a resultant mixture was dried at 60° C. for 1 hour under a windless condition.

Subsequently, after the drying, resultant particles were crushed (subjected to a particle sizing step) until the resultant particles passed through the JIS standard sieve having a mesh size of 710 μm, so that a comparative water-absorbing agent (3) was obtained. Properties of the obtained comparative water-absorbing agent (3) are shown in Table 4.

Example 3

Operations similar to those carried out in Comparative Example 3 were carried out except that a heated gaseous surface crosslinking agent was externally introduced so that ethylene glycol and propylene glycol in a hot air dryer for carrying out a heat treatment each had a gas density of 0.015 g/L at all times for not shorter than five minutes of the start of surface crosslinking, so that a water-absorbing agent (3) was obtained. Physical properties of the obtained water-absorbing agent (3) are shown in Table 4.

Comparative Example 4

The water-absorbing resin powder (C) obtained in Reference Example 3 was surface-crosslinked by the following process.

With respect to 100 parts by weight of the water-absorbing resin powder (C) obtained in Reference Example 3, 4.1 parts by weight of a surface crosslinking agent mixed solution containing 2-oxo-1,3-dioxolane, 1,2-propanediol, and ion exchanged water (in a mixing ratio (weight ratio) of 0.4:0.7:3.0) was added and mixed. In the mixing, a Loedige mixer (manufactured by Gerbrueder Ledige Maschibenbau GmbH) was used as a mixing apparatus. The water-absorbing resin powder (C) and the surface crosslinking agent mixed solution were mixed by spraying the surface crosslinking agent mixed solution by use of a spray nozzle (single-fluid hollow cone nozzle (1/4M-K-008) manufactured by H. IKEUCHI Co., Ltd.).

A resultant mixture was uniformly spread over a stainless-steel vat. The stainless-steel vat was left at rest in a dryer in which humidity was controlled at an atmospheric temperature of 197° C. and a dew point of 90° C., the atmospheric temperature and the dew point each having been measured by Humidity and Temperature Transmitter HMT337 (manufactured by VAISALA). Then, a heat treatment was carried out for 30 minutes.

After the heating, resultant particles were allowed to pass through a JIS standard sieve having a mesh size of 850 μm, so that comparative water-absorbing resin particles (4) having a surface and its vicinity which were crosslinked.

As to this surface crosslinking condition, a change in concentration of the surface crosslinking agent in the dryer was analyzed by collecting gas in the dryer per minute from the start of the surface crosslinking. As a result, 2-oxo-1,3-dioxolane and ethylene glycol, which is a degradation product of 2-oxo-1,3-dioxolane, had a total gas density of 0.007 g/L after 1 minute; 0.01 g/L after 2 minutes; 0.0067 g/L after 3 minutes; and 0.0054 g/L after 4 or more minutes, from the start of an increase in temperature of the water-absorbing resin powder (C).

Meanwhile, 1,2-propanediol had a gas density of 0.0073 g/L after 1 minute; 0.012 g/L after 2 minutes; 0.0067 g/L after 3 minutes; and 0.0054 g/L after 4 or more minutes, from the start of the increase in temperature of the water-absorbing resin powder (C).

To 100 parts by weight of the obtained comparative water-absorbing resin particles (4), an aluminum sulfate mixed solution containing a 27 mass % aqueous aluminum sulfate solution (8 weight % in terms of aluminum oxide), a 60 weight % aqueous sodium lactate solution, and 1,2-propylene glycol (in a mixing ratio of 1:0.3:0.025) was added. After the addition, a resultant mixture was dried at 60° C. for 1 hour under a windless condition.

Subsequently, after the drying, resultant particles were allowed to pass through the JIS standard sieve having a mesh size of 850 μm, so that a comparative water-absorbing agent (4) was obtained. Physical properties of the obtained comparative water-absorbing resin particles (4) and physical properties of the obtained comparative water-absorbing agent (4) are shown in Table 4.

Example 4

Operations similar to those carried out in Comparative Example 4 were carried out except that a heated gaseous surface crosslinking agent was externally introduced so that (i) a total gas density of 2-oxo-1,3-dioxolane and ethylene glycol, which is a degradation product of 2-oxo-1,3-dioxolane, in a dryer for carrying out a heat treatment and (ii) a gas density of 1,2-propanediol were each 0.0125 g/L at all times for not shorter than five minutes of the start of surface crosslinking, so that water-absorbing resin particles (4) and a water-absorbing agent (4) were obtained. Physical properties of the obtained water-absorbing resin particles (4) and physical properties of the obtained water-absorbing agent (4) are shown in Table 4.

Comparative Example 5

The water-absorbing resin powder (C) obtained in Reference Example 3 was used to carry out surface crosslinking with reference to Example 1 of Patent Literature 72 (the specification of U.S. Patent Application Publication No. 2011/0112252). This is specifically described below.

Approximately 100 g of the water-absorbing resin powder (C) obtained in Reference Example 3 was charged into a fluidized bed reactor having an internal diameter of 7 cm. In the reactor, carrier gas had a superficial velocity of 1 m/s. As the carrier gas, industrial nitrogen having a temperature of 160° C. was used. The water-absorbing resin powder (C) was dried in the reactor for 10 minutes.

Next, to the carrier gas, 1,2-propanediol was added upstream of the reactor at 160° C. (t=0). 1,2-propanediol had a gas density of approximately 20 millibars (≈20 hPa) in the carrier gas.

Physical properties of comparative water-absorbing resin particles (5) obtained by the above operations are shown in Table 4. As to this surface crosslinking condition, a water vapor density in the reactor after the elapse of 5 minutes from the start of the reaction was analyzed by collecting gas in the reactor. As a result, the water vapor density was 0.05 g/L.

Example 5

Operations similar to those carried out in Comparative Example 5 were carried out except that (i) a mixture in which 4.1 parts by weight of a surface crosslinking agent mixed solution containing 1,2-propanediol and ion exchanged water (in a mixing ratio (weight ratio) of 1.1:3.0) had been added to and mixed with 100 parts by weight of the water-absorbing resin powder (C) obtained in Reference Example 3 was charged into a fluidized bed reactor and (ii) 1,2-propanediol in the fluidized bed reactor had a gas density of 0.0125 g/L at all times for not shorter than five minutes of the start of surface crosslinking, so that water-absorbing resin particles (5) were obtained. Physical properties of the obtained water-absorbing resin particles (5) are shown in Table 4. As to this surface crosslinking condition, a water vapor density in the fluidized bed reactor after the elapse of 5 minutes from the start of the reaction was analyzed by collecting gas in the fluidized bed reactor. As a result, the water vapor density was 0.3 g/L.

Comparative Example 6

The water-absorbing resin powder (C) obtained in Reference Example 3 was continuously supplied to a humidifying and mixing apparatus at 55 kg/hr, and 2.26 kg/hr of a surface crosslinking agent mixed solution containing 2-oxo-1,3-dioxolane, 1,2-propanediol, and ion exchanged water (in a mixing ratio (weight ratio) of 0.4:0.7:3.0) was added to and mixed with the water-absorbing resin powder (C).

A humidified product obtained by the above operations was immediately heat-treated by use of a paddle dryer into which 55 Nm³/hr of dry air was introduced and which was adjusted so that 2-oxo-1,3-dioxolane and ethylene glycol, which is a degradation product of 2-oxo-1,3-dioxolane, had a total gas density of 0.004 g/L, and 1,2-propanediol had a gas density of 0.006 g/L, the 2-oxo-1,3-dioxolane, the ethylene glycol, and the 1,2-propanediol each having been present in a gas phase inside the paddle dryer.

Thereafter, to 100 parts by weight of comparative water-absorbing resin particles (6) that had been surface-crosslinked was being cooled by use of a paddle cooler, a mixed solution containing 0.80 parts by weight of a 27 weight % aqueous aluminum sulfate solution (8 weight % in terms of aluminum oxide), 0.134 parts by weight of a 60 weight % aqueous sodium lactate solution, and 0.016 parts by weight of propylene glycol was added. After the addition, a resultant mixture was dried at 60° C. for 1 hour under a windless condition.

Subsequently, after the drying, resultant particles were allowed to pass through a JIS standard sieve having a mesh size of 850 μm, so that a comparative water-absorbing agent (6) was obtained. Physical properties of the obtained comparative water-absorbing agent (6) are shown in Table 4.

Example 6

Operations similar to those carried out in Comparative Example 6 were carried out except that a paddle dryer for carrying out a heat treatment was adjusted so that (i) 10 Nm³/hr of dry air was introduced into the paddle dryer and (ii) 2-oxo-1,3-dioxolane and ethylene glycol, which is a degradation product of 2-oxo-1,3-dioxolane, had a total gas density of 0.011 g/L, and 1,2-propanediol had a gas density of 0.015 g/L, the 2-oxo-1,3-dioxolane, the ethylene glycol, and the 1,2-propanediol each having been present in a gas phase inside the paddle dryer, so that a water-absorbing agent (6) was obtained. Physical properties of the obtained water-absorbing agent (6) are shown in Table 4.

Reference Example 4

In the present Reference Example 4, a water-absorbing resin powder (D) that was particulate and had not been surface-crosslinked was obtained by carrying out polymerization, gel grinding, drying, pulverization, and classification with reference to Example 3 of Japanese Patent Application Publication, Tokukai, No. 2007-284675. This is specifically described below.

<Polymerization>

A solution (d 1) was prepared by mixing, in a 1 L container made of polypropylene resin, 293.1 g of acrylic acid, 1.1 g of polyethylene glycol diacrylate (average molecular weight: 522) as an internal crosslinking agent, 1.8 g of a 1 weight % aqueous diethylene triamine pentaacetate pentasodium solution as a chelating agent, and 3.6 g of a 1.0 weight % acrylic acid solution of IRGACURE (Registered Trademark) as a polymerization initiator. There was also prepared a solution (d2) in which 237.65 g of a 48.5 weight % aqueous sodium hydroxide solution and 251.82 g of ion exchanged water adjusted to have a temperature of 50° C.

To the solution (d 1) which had been stirred at 500 rpm by use of a magnetic stirrer chip having a length of 50 mm, 18 g of synthetic zeolite (manufactured by TOSOH CORPORATION, ZEOLUM A-4, 100 mesh-pass powder) was added. Then, the solution (d2) was quickly added to and mixed with a resultant mixture, so that an aqueous monomer solution (D) was obtained. A temperature of the aqueous monomer solution (D) rose to 102° C. due to heat of neutralization and heat of dissolution.

Next, at a point in time at which the temperature of the aqueous monomer solution (D) decreased to 97° C., 11 g of a 3 weight % aqueous sodium persulfate solution was added to the aqueous monomer solution (D). Immediately after being stirred for approximately 1 second, a resultant mixture was poured, in an atmospheric air open system, into a stainless-steel vat container having (i) a surface heated by use of a hot plate (manufactured by Iuchi Seieido Co., Ltd.; NEO HOTPLATE HI-1000) set at 130° C., (ii) an inner surface coated with Teflon (Registered Trademark), and a bottom surface of 250 mm×250 mm. The vat container has a bottom surface of 250 mm×250 mm, a top surface of 640 mm×640 mm, a height of 50 mm, and a trapezoidal central cross section, the top surface being opened.

While being poured into the stainless-steel vat container, the aqueous monomer solution (D) was irradiated with an ultraviolet ray by use of an ultraviolet irradiation device (TOSCURE 401, model name: HC-04131-B, lamp: H400L/2, manufactured by HARISON TOSHIBA LIGHTING Corporation) provided at a height of 600 mm from the bottom surface of the stainless-steel vat container.

Immediately after the aqueous monomer solution (D) was poured into the vat, static aqueous solution polymerization progressed while water vapor was being generated (polymerization starting temperature: 97° C.). A temperature of the polymerization reached a peak temperature within approximately 1 minute (peak temperature: 106° C.). After 3 minutes elapsed, ultraviolet irradiation was stopped, and a hydrogel-forming crosslinked polymer (hydrogel) (D) was taken out. Note that this series of operations was carried out in an atmospheric air open system.

<Gel Grinding>

After the hydrogel (D) taken out was cut with scissors into strips having a width of 30 mm, the strips were subjected to gel grinding by use of a meat chopper (manufactured by Iizuka Kogyo Co., Ltd., MEAT-CHOPPER TYPE: 12VR-400KSOX, die pore diameter: 9.5 mm, the number of pores: 18, die thickness: 8 mm) at a speed of input of the hydrogel of approximately 6 g/s while ion exchanged water was being added at 1.4 g/s, so that a grain-refined particulate hydrogel (D) was obtained.

<Drying, and Pulverization and Classification>

The particulate hydrogel (D) was spread over and placed on a woven wire having a mesh size of 850 μm, and was dried at 180° C. for 40 minutes by letting hot air through. Next, a dried polymer (D) obtained by the drying was pulverized by use of a roll mill (WML-type roll crusher, manufactured by Inoguchi Giken Ltd.) and then classified and blended by use of a JIS standard sieve having a mesh size of 850 μm.

By the above operations, a water-absorbing resin powder (D) was obtained which was ground to have an uneven shape, which had a weight average particle diameter (D50) of 461 μm, which contained, in an amount of 28 weight %, particles whose particle diameter was not less than 600 μm and less than 850 μm, and contained, in an amount of 2.2 weight %, particles whose particle diameter was less than 150 μm, and which had a logarithmic standard deviation (σζ) of 0.364 and a solid content of 96 weight %. Physical properties of the obtained water-absorbing resin powder (D) are shown in Table 1.

Comparative Example 7

A surface crosslinking agent solution containing 0.3 parts by weight of 1,4-butanediol, 0.5 parts by weight of propylene glycol, and 2.7 parts by weight of deionized water was uniformly mixed with 100 parts by weight of the water-absorbing resin powder (D) obtained in Reference Example 4.

The water-absorbing resin powder (D) with which the surface crosslinking agent solution had been mixed was heat-treated for any time by use of a heating apparatus provided with a stirring blade and a jacket (jacket temperature: 210° C.).

The water-absorbing resin powder (D), which had been heat-treated, was allowed to pass through a JIS standard sieve having a mesh size of 850 μm, so that comparative water-absorbing resin particles (7) that had been surface-crosslinked were obtained. Physical properties of the obtained comparative water-absorbing resin particles (7) are shown in Table 5.

As to this surface crosslinking condition, a change in concentration of the surface crosslinking agent in the heating apparatus was analyzed by collecting gas in the heating apparatus per minute from the start of the surface crosslinking. As a result, 1,4-butanediol had a gas density of 0.0061 g/L after 1 minute; 0.009 g/L after 2 minutes; 0.0077 g/L after 3 minutes; and 0.0048 g/L after 4 or more minutes, from the start of an increase in temperature of the water-absorbing resin powder (D).

Meanwhile, propylene glycol had a gas density of 0.0075 g/L after 1 minute; 0.0125 g/L after 2 minutes; 0.0075 g/L after 3 minutes; and 0.005 g/L after 4 or more minutes, from the start of the increase in temperature of the water-absorbing resin powder (D).

Comparative Example 8

Operations similar to those carried out in Comparative Example 7 were carried out except that a heating apparatus was adjusted so that 1,4-butanediol had a gas density of 0.01 g/L for not shorter than five minutes and propylene glycol had a gas density of 0.01 g/L for not shorter than five minutes, the 1,4-butanediol and the propylene glycol each having been present in a gas phase inside the heating apparatus, so that comparative water-absorbing resin particles (8) were obtained. Physical properties of the obtained comparative water-absorbing resin particles (8) are shown in Table 5.

Comparative Example 9

In the present Comparative Example 9, a water-absorbing resin powder (E) that was particulate and had not been surface-crosslinked was obtained by carrying out polymerization, gel grinding, drying, pulverization, and classification with reference to Example 3 of PCT/JP2014/07620. By use of the water-absorbing resin powder (E) thus obtained, operations similar to those carried out in Comparative Example 3 were carried out by changing a heat treatment time to 50 minutes, so that a comparative water-absorbing agent (9) was obtained. Physical properties of the obtained comparative water-absorbing agent (9) are shown in Table 6.

Example 7

In the present Example 7, a water-absorbing resin powder (E) that was particulate and had not been surface-crosslinked was obtained by carrying out polymerization, gel grinding, drying, pulverization, and classification with reference to Example 3 of PCT/JP2014/07620. By use of the water-absorbing resin powder (E) thus obtained, operations similar to those carried out in Example 3 were carried out by changing a heat treatment time to 50 minutes, so that a water-absorbing agent (7) was obtained. Physical properties of the obtained water-absorbing agent (7) are shown in Table 6.

Comparative Example 10

In the present Comparative Example 10, a water-absorbing resin powder (F) that was particulate and had not been surface-crosslinked was obtained by carrying out polymerization, gel grinding, drying, pulverization, and classification with reference to Example 11 of PCT/JP2014/07620. By use of the water-absorbing resin powder (F) thus obtained, operations similar to those carried out in Comparative Example 3 were carried out by changing a heat treatment time to 50 minutes, so that a comparative water-absorbing agent (10) was obtained. Physical properties of the obtained comparative water-absorbing agent (10) are shown in Table 6.

Example 8

In the present Example 8, a water-absorbing resin powder (F) that was particulate and had not been surface-crosslinked was obtained by carrying out polymerization, gel grinding, drying, pulverization, and classification with reference to Example 11 of PCT/JP2014/07620. By use of the water-absorbing resin powder (F) thus obtained, operations similar to those carried out in Example 3 were carried out by changing a heat treatment time to 50 minutes, so that a water-absorbing agent (8) was obtained. Physical properties of the obtained water-absorbing agent (8) are shown in Table 6.

Comparative Example 11

In the present Comparative Example 11, a water-absorbing resin powder (G) that was particulate and had not been surface-crosslinked was obtained by carrying out polymerization, gel grinding, drying, pulverization, and classification with reference to Example 19 of PCT/JP2014/07620. By use of the water-absorbing resin powder (G) thus obtained, operations similar to those carried out in Comparative Example 3 were carried out by changing a heat treatment time to 50 minutes, so that a comparative water-absorbing agent (11) was obtained. Physical properties of the obtained comparative water-absorbing agent (11) are shown in Table 6.

Example 9

In the present Example 9, a water-absorbing resin powder (G) that was particulate and had not been surface-crosslinked was obtained by carrying out polymerization, gel grinding, drying, pulverization, and classification with reference to Example 19 of PCT/JP2014/07620. By use of the water-absorbing resin powder (G) thus obtained, operations similar to those carried out in Example 3 were carried out by changing a heat treatment time to 50 minutes, so that a water-absorbing agent (9) was obtained. Physical properties of the obtained water-absorbing agent (9) are shown in Table 6.

TABLE 1

| | | CRCs [g/g] | FSR [g/g/s] | Vortex [sec] | Bulk specific gravity [g/cm$^3$] | D50 [μm] | σξ [−] | Solid content [wt %] |
|---|---|---|---|---|---|---|---|---|
| Reference Example 1 | Water-absorbing resin powder (A) | 34.5 | 0.35 | 29.3 | 0.66 | 446 | 0.39 | 97 |
| Reference Example 2 | Water-absorbing resin powder (B) | 35.2 | 0.38 | 25.4 | 0.63 | 460 | 0.39 | 97 |
| Reference Example 3 | Water-absorbing resin powder (C) | 31.6 | 0.36 | 28.0 | 0.67 | 350 | 0.33 | 97 |
| Reference Example 4 | Water-absorbing resin powder (D) | 33.1 | 0.33 | 32.0 | 0.54 | 461 | 0.36 | 96 |

TABLE 2

| | | CRCs [g/g] | FSR [g/g/s] | Vortex [sec] | Bulk specific gravity [g/cm$^3$] | D50 [μm] | AAP [g/g] | SFC [$10^{-7} \cdot cm^3 \cdot s \cdot g^{-1}$] | Salt Tolerance Index [CRCdw/CRCs] | Formula (2)* |
|---|---|---|---|---|---|---|---|---|---|---|
| Comparative Example 1 | Comparative water-absorbing agent (1) | 27.2 | 0.36 | 28.0 | 0.67 | 432 | 23.8 | 114 | 6.67 | 5.86 |
| Example 1 | Water-absorbing agent (1) | 27.1 | 0.36 | 28.0 | 0.67 | 437 | 24.8 | 158 | 5.51 | 5.81 |

*Formula (2): calculated value of 0.49 × CRCs − 7.47

TABLE 3

|  |  | CRCs [g/g] | FSR [g/g/s] | Vortex [sec] | Bulk specific gravity [g/cm³] | D50 [μm] | AAP [g/g] | SFC [$10^{-7} \cdot cm^3 \cdot s \cdot g^{-1}$] | Salt Tolerance Index [CRCdw/CRCs] | Formula (2)* |
|---|---|---|---|---|---|---|---|---|---|---|
| Comparative Example 2 | Comparative water-absorbing agent (2) | 27.4 | 0.39 | 24.1 | 0.66 | 462 | 24.4 | 130 | 6.67 | 5.96 |
| Example 2 | Water-absorbing agent (2) | 27.2 | 0.38 | 25.4 | 0.66 | 459 | 24.9 | 154 | 5.68 | 5.86 |

*Formula (2): calculated value of 0.49 × CRCs − 7.47

TABLE 4

|  |  | CRCs [g/g] | FSR [g/g/s] | Vortex [sec] | Bulk specific gravity [g/cm³] | D50 [μm] | AAP [g/g] | SFC [$10^{-7} \cdot cm^3 \cdot s \cdot g^{-1}$] | Salt Tolerance Index [CRCdw/CRCs] | Formula (2)* |
|---|---|---|---|---|---|---|---|---|---|---|
| Comparative Example 3 | Comparative water-absorbing agent (3) | 27.1 | 0.36 | 28.0 | 0.67 | 367 | 24.1 | 90 | 6.73 | 5.81 |
| Example 3 | Water-absorbing agent (3) | 27.3 | 0.35 | 29.3 | 0.67 | 371 | 24.7 | 142 | 5.59 | 5.91 |
| Comparative Example 4 | Comparative water-absorbing resin particles (4) | 27.5 | 0.36 | 28.0 | 0.67 | 368 | 23.9 | 53 | 6.24 | 6.01 |
|  | Comparative water-absorbing agent (4) | 27.2 | 0.37 | 26.7 | 0.67 | 369 | 23.6 | 97 | 6.15 | 5.86 |
| Example 4 | Water-absorbing resin particles (4) | 27.4 | 0.36 | 28.0 | 0.67 | 367 | 24.8 | 72 | 5.67 | 5.96 |
|  | Water-absorbing agent (4) | 27.2 | 0.36 | 28.0 | 0.67 | 368 | 24.5 | 143 | 5.64 | 5.86 |
| Comparative Example 5 | Comparative water-absorbing resin particles (5) | 26.9 | 0.35 | 29.3 | 0.65 | 366 | 23.6 | 43 | 6.89 | 5.71 |
| Example 5 | Water-absorbing resin particles (5) | 27 | 0.36 | 28.0 | 0.66 | 370 | 24.5 | 78 | 5.68 | 5.76 |
| Comparative Example 6 | Comparative water-absorbing agent (6) | 27.6 | 0.38 | 25.4 | 0.66 | 365 | 23.7 | 78 | 6.58 | 6.05 |
| Example 6 | Water-absorbing agent (6) | 27.7 | 0.37 | 26.7 | 0.65 | 372 | 24.7 | 113 | 5.53 | 6.10 |

*Formula (2): calculated value of 0.49 × CRCs − 7.47

TABLE 5

|  |  | CRCs [g/g] | FSR [g/g/s] | Vortex [sec] | Bulk specific gravity [g/cm³] | D50 [μm] | AAP [g/g] | SFC [$10^{-7} \cdot cm^3 \cdot s \cdot g^{-1}$] | Salt Tolerance Index [CRCdw/CRCs] | Formula (2)* |
|---|---|---|---|---|---|---|---|---|---|---|
| Comparative Example 7 | Comparative water-absorbing resin particles (7) | 27.2 | 0.33 | 32.0 | 0.54 | 461 | 24.2 | 53 | 3.84 | 5.86 |
| Comparative Example 8 | Comparative water-absorbing resin particles (8) | 27.2 | 0.32 | 33.3 | 0.53 | 460 | 25 | 77 | 3.09 | 5.86 |

*Formula (2): calculated value of 0.49 × CRCs − 7.47

TABLE 6

| | | CRCs [g/g] | FSR [g/g/s] | Vortex [sec] | Bulk specific gravity [g/cm³] | D50 [μm] | AAP [g/g] | SFC [$10^{-7} \cdot cm^3 \cdot s \cdot g^{-1}$] | Salt Tolerance Index [CRCdw/CRCs] | Formula (2)* |
|---|---|---|---|---|---|---|---|---|---|---|
| Comparative Example 9 | Comparative water-absorbing agent (9) | 27.5 | 0.31 | 38.1 | 0.6 | 365 | 24.2 | 121 | 6.73 | 6.01 |
| Comparative Example 10 | Comparative water-absorbing agent (10) | 30.5 | 0.29 | 41.2 | 0.62 | 457 | 25.3 | 53 | 7.96 | 7.48 |
| Comparative Example 11 | Comparative water-absorbing agent (11) | 34.2 | 0.3 | 39.0 | 0.63 | 458 | 22.5 | 10 | 10.08 | 9.29 |
| Example 7 | Water-absorbing agent (7) | 27.6 | 0.32 | 37.3 | 0.6 | 363 | 24.5 | 132 | 5.69 | 6.05 |
| Example 8 | Water-absorbing agent (8) | 30.5 | 0.3 | 39.2 | 0.62 | 459 | 25.9 | 64 | 7.24 | 7.48 |
| Example 9 | Water-absorbing agent (9) | 34.3 | 0.31 | 37.9 | 0.61 | 455 | 23.2 | 16 | 9.21 | 9.34 |

*Formula (2): calculated value of 0.49 × CRCs − 7.47

As shown in "Water-absorbing agent (1)" to "Water-absorbing agent (3)" in respective Tables 2 to 4, and FIG. 1, in a case where by adjusting a surface crosslinking agent, which is present in a gas phase inside a heat treatment machine (heating apparatus) during surface crosslinking, so that a surface crosslinking agent C2 compound and a surface crosslinking agent C3 compound each have a gas density that is maintained at at least 0.01 g/L at all times for not shorter than five minutes of the start of a heat treatment, the surface crosslinking agent is prevented from evaporating at an early stage of the surface crosslinking, it is possible, regardless of a method for producing a water-absorbing resin powder before surface crosslinking, to produce a water-absorbing agent which simultaneously achieves a water absorbing speed (high FSR), a fluid retention capacity under load (high AAP), liquid permeability (high SFC), and salt tolerance.

As shown in "Water-absorbing agent (4)" to "Water-absorbing agent (6)" in Table 4, the present invention is a water-absorbing agent production method that is more excellent in simultaneous achievement of a water absorbing speed (high FSR), a fluid retention capacity under load (high AAP), and liquid permeability (high SFC) as compared with conventional surface crosslinking methods such as a method for carrying out surface crosslinking in an environment of a high dew point by introducing only water vapor into a heat treatment machine and a method for carrying out surface crosslinking without carrying out a humidifying and mixing process and by use of only carrier gas containing a waterless surface crosslinking agent (Patent Literature 72).

As shown in "Water-absorbing agent (6)" in Table 4, a method for adjusting a concentration of a surface crosslinking agent in a heat treatment machine is not necessarily external introduction of a heated vaporous surface crosslinking agent. In the case of a continuous producing machine, the effect of the present invention can be obtained also in a case where (i) a volume flow rate of dry air to be introduced into a heat treatment machine is controlled so that a ratio of the volume flow rate to a weight of a water-absorbing resin to be heat-treated is 200 Nm³/ton or less and (ii) a surface crosslinking agent, which is present in a gas phase part of an inside of the heat treatment machine, is adjusted so that a surface crosslinking agent C2 compound and a surface crosslinking agent C3 compound each have a gas density of at least 0.01 g/L at all times for not shorter than five minutes of the start of a heat treatment.

Meanwhile, as shown in "Comparative water-absorbing resin particles (7)" and "Comparative water-absorbing resin particles (8)" in Table 5, a technique of Patent Literature 68 for adding a water-insoluble solid matter such as zeolite during polymerization also makes it possible to simultaneously achieve a water absorbing speed (high FSR), a fluid retention capacity under load (high AAP), and liquid permeability (high SFC). Note, however, that employment of this technique, which causes a reduction in bulk specific gravity, in sanitary products such as disposable diapers and sanitary napkins increases a volume of a water-absorbing agent that accounts for an absorbent article having a predetermined level of absorbing ability, so that thin sanitary products cannot be produced.

Further, as shown in Table 6, in a case where by adjusting a surface crosslinking agent, which is present in a gas phase inside a heat treatment machine during surface crosslinking, so that a surface crosslinking agent C2 compound and a surface crosslinking agent C3 compound each have a gas density that is maintained at at least 0.01 g/L at all times for not shorter than five minutes of the start of a heat treatment, the surface crosslinking agent is prevented from evaporating at an early stage of the surface crosslinking, it is possible, in a broad range of CRC, to produce a water-absorbing agent which simultaneously achieves a water absorbing speed (high FSR), a fluid retention capacity under load (high AAP), liquid permeability (high SFC), and salt tolerance.

INDUSTRIAL APPLICABILITY

The present invention is preferably usable for, for example, (i) a water-absorbing agent to be used in sanitary products such as disposable diapers, sanitary napkins, and incontinence pads and (ii) a method for producing the water-absorbing agent.

The invention claimed is:
1. A polyacrylic acid (salt)-based water-absorbing agent whose surface and its vicinity are crosslinked by an organic surface crosslinking agent, the polyacrylic acid (salt)-based water-absorbing agent prepared by a method comprising:
   heat treating a mixture containing water, a surface crosslinking agent and a water-absorbing resin powder,
   wherein the water-absorbing resin powder is heat treated for at least five minutes from a start of raising a temperature with a gas density of a surface crosslinking agent C2 compound and/or a surface crosslinking agent C3 compound being at least 0.01 g/L, where the surface crosslinking agent C2 compound is a compound, of which longest carbon chain has 2 carbons, containing a total number of carbons of 3 or less, with either one of an oxygen atom or a nitrogen atom being bonded to each of carbon atoms at both ends of the carbon chain; and the surface crosslinking agent C3 compound is a compound, of which longest carbon chain has 3 carbons, containing a total number of carbons of 4 or less, with either one of an oxygen atom or a nitrogen atom being bonded to each of different carbon atoms on the carbon chain; and the gas density is a weight of the surface crosslinking agent C2 compound or the surface crosslinking agent C3 compound that is contained per unit volume of a non-condensable gas;

wherein the polyacrylic acid (salt)-based water-absorbing agent is characterized by satisfying the following (A)-(D):

(A) Free Swell Rate (FSR) of at least 0.35 g/g/s, or Absorption Time (Vortex) of 36 seconds or less;

(B) Absorption Against Pressure (AAP) of at least 20 g/g;

(C) Salt Tolerance Index represented by the following Formula 1 satisfying the following Formula 2:

Salt Tolerance Index=(CRCdw)/(CRCs)  (Formula 1)

where CRCdw is a centrifuge retention capacity (unit; g/g) for deionized water (dw), and CRCs is a centrifuge retention capacity (unit; g/g) for a 0.9 weight % saline, Salt Tolerance Index≤0.49×CRCs−7.47  (Formula 2); and (D) Bulk Specific Gravity of 0.55 to 0.70 $g/cm^3$.

2. The polyacrylic acid (salt)-based water-absorbing agent according to claim 1, wherein the Absorption Time (Vortex) is 30 seconds or less.

3. The polyacrylic acid (salt)-based water-absorbing agent according to claim 1, wherein the Salt Tolerance Index is 5.7 or less.

4. The polyacrylic acid (salt)-based water-absorbing agent according to claim 1, wherein the Absorption Against Pressure (AAP) is at least 23.5 g/g.

5. The polyacrylic acid (salt)-based water-absorbing agent according to claim 1, further satisfying: (E) Saline Flow Conductivity (SFC) of at least $10\times10^{-7} \cdot cm^3 \cdot s \cdot g^{-1}$.

6. The polyacrylic acid (salt)-based water-absorbing agent according to claim 5, wherein the Saline Flow Conductivity (SFC) is at least $30\times10^{-7}\ cm^3 \cdot s \cdot g^{-1}$.

* * * * *